US005712044A

United States Patent [19]

Fanselow et al.

[11] Patent Number: 5,712,044
[45] Date of Patent: Jan. 27, 1998

[54] MEDICAL DEVICE ASSEMBLIES CONSTRUCTED FROM MULTILAYERED FILMS

[75] Inventors: Dan L. Fanselow, White Bear Lake; Raymond L. Ferguson; Walton J. Hammar, both of St. Paul; Lester B. Odegaard, Afton; Daryl D. Dressler, St. Paul; Jon M. Nornberg, Woodbury; Ching-Long Tsai, Woodbury; John H. Ko, Woodbury; Craig S. Chamberlain, Woodbury; Charlotte M. Palmgren, Lake Elmo, all of Minn.

[73] Assignee: Minnesota Mining and Manufacturing Company, St. Paul, Minn.

[21] Appl. No.: 465,407

[22] Filed: Jun. 5, 1995

Related U.S. Application Data

[62] Division of Ser. No. 103,082, Aug. 6, 1993, abandoned.

[51] Int. Cl.⁶ ........................................ B32B 27/00
[52] U.S. Cl. ..................... 428/515; 428/510; 428/519; 428/522
[58] Field of Search ................. 428/510, 515, 428/519, 522; 604/132, 153, 247; D24/127

[56] References Cited

U.S. PATENT DOCUMENTS

| | | | |
|---|---|---|---|
| 3,561,493 | 2/1971 | Maillard | 138/141 |
| 4,236,880 | 12/1980 | Archibald | 417/478 |
| 4,286,597 | 9/1981 | Gajewski et al. | 128/272 |
| 4,298,714 | 11/1981 | Levin et al. | 525/330 |
| 4,382,753 | 5/1983 | Archibald | 417/479 |
| 4,391,600 | 7/1983 | Archibald | 604/153 |
| 4,410,322 | 10/1983 | Archibald | 604/153 |
| 4,574,173 | 3/1986 | Bennett | 219/10.53 |
| 4,627,844 | 12/1986 | Schmitt | 604/264 |
| 4,702,963 | 10/1987 | Phillips et al. | 428/480 |
| 4,816,343 | 3/1989 | Mueller et al. | 428/480 |
| 5,193,913 | 3/1993 | Rosenbaum | 383/113 |
| 5,203,943 | 4/1993 | Nornberg et al. | 156/245 |
| 5,245,151 | 9/1993 | Chamberlain et al. | 219/10.57 |
| 5,254,824 | 10/1993 | Chamberlain et al. | 219/10.57 |

FOREIGN PATENT DOCUMENTS

| | | |
|---|---|---|
| 187083 | 7/1992 | China . |
| 40189 | 7/1992 | China . |
| 0 179 181 | 1/1985 | European Pat. Off. . |
| 0 397 321 A1 | 11/1990 | European Pat. Off. . |
| 0 503 794 A1 | 9/1992 | European Pat. Off. . |
| 41 00 350 A1 | 4/1992 | Germany . |
| WO 87/05563 | 9/1987 | WIPO . |
| WO 93/11655 | 6/1993 | WIPO . |
| WO 93/11938 | 6/1993 | WIPO . |
| WO 93/23093 | 11/1993 | WIPO . |

OTHER PUBLICATIONS

*Encyclopedia of Polymer Science and Engineering*, vol. 17, pp. 50–51, 1989.
*Encyclopedia of Polymer Science and Engineering*, vol. 7, pp. 106–127, 1987.
Brochure—3M HealthCare, "Infusion Pump Sets," Aug. 1989.
Brochure—3M HealthCare, "A VI Infusion Pump Sets," 1991.
Brochure—3M HealthCare, "A VI Infusion Pump Sets 8C Series," 1991.

*Primary Examiner*—Melvyn I. Marquis
*Assistant Examiner*—D. Aylward

[57] ABSTRACT

Multilayered film and film based assembly which are environmentally-compatible, and which exhibit one or more desirable characteristics of polyvinyl chloride (PVC) film and film based assemblies, such as clarity, flexibility and toughness, but without the environmental and health hazards associated with PVC materials, are provided. Also provided is a method of preparing such film and film based assembly.

16 Claims, 4 Drawing Sheets

MEDICAL DEVICE ASSEMBLIES CONSTRUCTED FROM MULTILAYERED FILMS

This is a division of application Ser. No. 08/103,082 filed Aug. 6, 1993, abandoned.

FIELD OF THE INVENTION

This invention relates to multilayered films and film based assemblies, such as medical pump cassettes, which are suitable to replace conventional polyvinyl chloride (PVC) films and assemblies, but without the environmental and health hazards associated with PVC materials. Further, this invention also relates to medical devices such as intravenous fluid administration sets made with PVC-free materials, which may include such film based assemblies along with other components.

BACKGROUND OF THE INVENTION

Polyvinyl chloride (PVC) based films and film based assemblies are used in numerous medical products. However, PVC is viewed as hazardous to both the environment and to personal health. Incineration of PVC results in the release of hydrochloric acid (HCl), and PVC is viewed as a major contributor to HCl in incinerator flue gases. Also, PVC is suspected of contributing to polychlorinated dibenzodioxin and furan toxins formed during incineration. Levels of these toxins are up to three times greater in medical infectious waste as compared to municipal waste streams. In addition to incineration concerns, exposure to di-2-ethylhexyl phthalate (DEHP), a common plasticizer used with PVC, may present a number of health related concerns, including reduced blood platelet efficacy and potential links to liver cancer.

Despite these concerns, PVC-based films and film based assemblies, continue to be the material of choice in scientific and medical applications. See, e.g., *Encyclopedia of Polymer-Science and Technology*, Vol. 17, pg. 50 (1989). The continued use of PVC materials is due, at least in part, to PVC's attractive qualities, including flexibility; toughness; resistance to UV light, solvents, cuts, scratches, and acids; clarity or opaqueness as required; and low cost. In addition, PVC's characteristics can be modified through the addition of various additives, such as plasticizers, colorants, and the like. For example, U.S. Pat. No. 4,298,714 discloses a modified PVC material with reduced hydrophilicity due to the addition of various thiol-group compounds to the PVC backbone.

Other thermoplastic polymers have been used to form single-layer films and film based assemblies. For example, low-density polyethylene, high density polyethylene, polypropylene, ethylene vinyl acetate, and polybutylene have all been used to form single-layer films and film based assemblies. *Encyclopedia of Polymer Science and Technology*, ibid., pp. 50–51. Further, films developed for replacement of PVC are often made of polyolefins. Polyolefins have low surface energies and are often difficult to bond with conventional adhesives or solvents. Consequently, none of these polymer materials has been successfully used to provide films and film based assemblies with the advantageous characteristics needed to serve as environmentally compatible replacements for PVC-based materials.

The problem is particularly acute with respect to tubing assemblies with cassettes used in connection with infusion pumps for metering IV fluids to a living patient. Cassettes, for example as taught in U.S. Pat. No. 4,236,880 to Archibald, must be highly flexible so as to deform in the manner of a rolling diaphragm when pressed by a pumping piston. They must additionally be tough enough to withstand repeated deformation for extended periods of time: 72 continuous hours is a typical institutional requirement among U.S. hospitals. Such cassettes are prepared by compression blow molding such that the material must be able to form a secure heat bond during the fabrication.

In addition to continued environmental incompatibility, these films and film based assemblies tend to delaminate during continuous usage. To avoid delamination problems, U.S. Pat. No. 3,561,493 provides a multilayered film in which the inside and outside layers are welded together by a precompounded layer of the two different polymers. However, chlorine-containing polymers, such as PVC, are still considered best for use in such films and film based assemblies.

To date, no films and film based assemblies exist which provide the advantageous characteristics of PVC materials, and yet are environmentally compatible upon disposal.

Therefore, there is a need for films and film based assemblies that can be utilized in a wide range of both medical and nonmedical products, and that can serve as replacements for PVC-based materials. There is a need for elements of medical devices such as IV infusion therapy sets which are environmentally compatible, and yet capable of satisfying the challenging requirements. Specifically, there is a need for PVC replacement cassettes, IV sets and medical films which are extremely flexible, yet tough enough to endure their intended use. They must be capable of being heat bonded, must be visually transparent, as well as solvent and UV light resistant, and capable of being made for a relatively low cost.

SUMMARY OF THE INVENTION

The present invention is directed to a multilayered film, a film based medical device assembly such as a medical cassette and methods for formation of the film and the film based medical device assembly.

The film is the building block component for the medical device assembly. The film has at least a core layer, an outside surface layer and an inside surface layer composed at least of chlorine-free thermoplastic polymers. The film has the capability of bonding to itself under heat conditions before the film core can distort substantially. Further the film is capable of being expanded at least in part under heat and pressure without failure of film integrity, flexibility and resilience. In preferred embodiments, an optional divider layer or layers is present within the core layer. In other embodiments, the core layer can also act as one of the surface layers.

The core layer is composed of at least one chlorine-free, first thermoplastic polymer, or a mixture of such first thermoplastic polymers, or a mixture of such first thermoplastic polymers with other substances and polymers. The outside surface layer is composed of at least one chlorine-free, second thermoplastic polymer, or a mixture of such second thermoplastic polymers, or a mixture of such second thermoplastic polymers with other substances and polymers. The inside surface layer is composed of at least one chlorine-free third thermoplastic polymer, or a mixture of such third thermoplastic polymers, or a mixture of such third thermoplastic polymers with other substances or polymers. The additional internal layers may most conveniently be composed at least of one of the first, second and third thermoplastic polymers or a mixture of such thermoplastic polymers alone or with other substances and polymers. Also such additional internal layers may be, but preferably are not, composed of halogen containing polymers such as polyvinyl chloride or polyfluorocarbons.

The first thermoplastic polymer has a flexibility that mimics or is greater than that of the polyvinyl chloride used to make medical grade film. In particular, it has a flexibility substantially needed to achieve film functions ranging from a capability to flex and recover, to a capability to be expanded without failure or deformity. More specifically, the first thermoplastic polymer has a flexibility that is measured as a Young's modulus that substantially mimics or is less than that of polyvinyl chloride film used for medical applications. Preferably, the first thermoplastic polymer Young's modulus ranges from about 10 to about 60 MPa (megaPascals), more preferably from about 10 to about 50 MPa especially preferably from about 15 to about 40 MPa.

The second thermoplastic polymer is tough and has an abrasion resistance that substantially mimics that of PVC used for medical film. It has a Young's modulus up to about ten times the Young's modulus of the first thermoplastic polymer. Preferably this ratio is up to a maximum of about seven times, more preferably, in a range of from about equal to, up to about three times, the Young's modulus of the first thermoplastic polymer. Especially preferably, this ratio is greater than, up to about three times the Young's modulus of the first thermoplastic polymer. Preferably, the Young's modulus of embodiments of the second thermoplastic polymer ranges from about 15 to about 300 MPa, more preferably from about 15 to 150 MPa.

The third thermoplastic polymer is able to form a strong heat seal to itself or like materials. It contains essentially no medically harmful substances that can be extracted or leached into an aqueous or organic based fluid stream and it will not absorb medications. It is preferred that the third thermoplastic polymer is capable of adding to the tensile strength of the composite film. It is also preferred that the third thermoplastic polymer has a Young's modulus within the general and preferred ranges given above for the second thermoplastic polymer.

Any thermoplastic polymer having the appropriate characteristics described above is appropriate for use as the first, second or third thermoplastic polymer. Generally, the first, second and third thermoplastic polymers have backbones of any configuration and chemical structure that will maintain the foregoing characteristics and thermoplasticity during multilayered film based assembly formation. Backbone configurations include but are not limited to linear, random, cross-linked, grafted, block, crystalline-amorphous domains, pseudo-cross-linked and ionomeric. Backbone chemical structures include polyolefin, polyester, polyurethane, while specific polyolefins include polyethylene/polyvinyl alcohol, polyethylene/polyvinyl acetate, polyacrylates, polymethacrylates, and polyvinyl acetates. Preferred thermoplastic polymers include the polymers of olefin monomers or copolymers of olefin monomers and substituted olefin monomers. Especially preferred olefin monomers include C2 to C4 mono-unsaturated alkenes and especially preferred substituted olefin monomers include C4 to C14 mono-unsaturated alkenes, C8 to C14 aryl alkenes, and C2 to C6 mono-unsaturated alkenes having moieties selected from the group consisting of acetoxy, carboxy, oxyalkanoyl, and alkoxycarbonyl of 1 to 6 carbons in the alkoxy group. The use of such a thermoplastic polymer as a first, second or third thermoplastic polymer depends but is not limited to the percent of substituted olefin monomer present in the polymer, the degree of regular molecular orientation achieved by the polymer, the degree of cross-linking, pseudo-cross-linking or ionomericity present, the backbone configurations mentioned above, the degree of the three dimensional rotation allowed by the chemical backbone structure, the degree of crystallinity and the nature of the monomer constituting the majority of the polymerized unit in the polymer.

The first thermoplastic polymer is flexible and soft. The second thermoplastic polymer is tough. The third thermoplastic polymer is preferably but not necessarily tough. The first thermoplastic polymer provides a film core with conformability and elasticity. The second thermoplastic polymer provides an outside surface layer with abrasion protection and non-stick release. The third thermoplastic polymer provides an inside surface layer with tensile strength and heat sealing ability. The thermoplastic polymers for the optional divider layer provide dimensional stability and tensile strength. In cooperation, the surface and core layers provide a multilayer film and film based assembly that are approximately as flexible, elastic, resilient and strong as, and in preferred embodiments exceed those characteristics of, PVC films and film based assemblies. The multilayer film is also as durable and scratch/abrasion resistant as PVC.

The multilayer film can have several configurations including three layer, five layer and megamulti (more than five) layer configurations. In all configurations, the outside surface, inside surface and divider layers are united or contiguously attached to the core layer. In the three layer configuration, the core layer is sandwiched between inside and outside surface layers. In the preferred five layer configuration, the inside, outside and core layers are constructed as in the three layer configuration. In addition, the divider layer is placed in approximately the middle of the core layer so as to divide the core layer into two parts. The divider layer in this configuration acts to further stabilize the core layer during formation of an assembly from a film.

In preferred embodiments, the core layer will be composed of a copolymer of an olefin and a substituted olefin and in particularly preferred embodiments, the copolymer can be an ethylene-vinyl acetate copolymer, an ethylene-butene copolymer, an ethylene-methyl acrylate copolymer, a very low modulus ionomer, and combinations thereof.

In preferred embodiments, the outside surface layer will be a non-stick or release olefin copolymer. A copolymer of ethylene and 1-octene or of ethylene and methyl acrylate is considered particularly suitable.

In preferred embodiments, the inside surface layer will be composed of an ionomeric copolymer. A copolymer of ethylene and methacrylic acid-metal cation salt is considered particularly suitable.

The film based assembly according to the invention is usually formed from two sheets of the multilayered film. The assembly is constructed to function in the capacity of, and to have characteristics similar to those of, a medical device made of a PVC composition. In a preferred embodiment, the film based assembly is a medical fluid bag, a flexible plastic drug container, or a medical pump cassette with molded-in fluid channels and pumping bubbles. The outside surface layer of the film based assembly provides a tough, protective coating for the assembly while the core layer provides the needed elasticity and flexibility. The inside surface layer provides not only toughness but also is particularly adapted for heat bonding. The optional divider layer provides additional dimensional stability and high precision formation during heat molding and sealing.

The invention is also directed to a method of forming a film based assembly. Such a method involves several steps, including forming a film as a sheet material by coextruding the first, second and third and optional divider thermoplastic polymers as contiguous united layers.

In a second step, the molded portion of the assembly is produced by molding a plurality of the sheets in a compression blow mold having at least two mold halves with at least one having internal cavities. In a preferred embodiment, two sheets of the film are placed between the mold halves with their outside surface layers facing the mold halves and their inside surface layers positioned to touch each other when the mold is closed. The molded portion of the assembly is molded by closing the mold halves and applying pressure and heat to the sheets while applying gas pressure to the portions of the sheets within the internal cavities.

The molded portion of the assembly is then optionally bonded to its connective or other preformed components, which in many cases will be polymeric tubing. In preferred embodiments, the polymeric tubing will also be fabricated from chlorine-free polymers. This bonding may be done by appropriate adhesives, or may advantageously be performed by applying a mixture of a polymeric binder and susceptor particles to the connective components, placing the connective components and the molded portion of the assembly in contact with each other, and subjecting the combination to electromagnetic radiation. The susceptor particles then absorb the electromagnetic radiation and generate heat. This heat melts the polymeric binder material and bonds the assembly together.

When adhesive bonding is performed, some otherwise appropriate adhesives have little green strength, and in such cases, susceptor particles may be mixed with the adhesive, and the adhesive exposed to electromagnetic radiation to speed the cure and to enhance the green strength.

The invention is also directed to a method for bonding together at least one tube and at least one plastic fluid transporting component. The method includes the steps of coating at least a portion of one of the tube and the plastic fluid transporting component (article) with the polymeric binder with susceptor particles wherein that portion is an area of the article to be bonded to the other article. The areas of the articles to be bonded together are contacted. Those contacted areas are irradiated with electromagnetic radiation. The susceptor particles absorb the radiation and cause local melting of the adhesive and/or plastic material and hence bonding or sealing together. The susceptor particles can be ferrite powders, metal powders, carbon black, graphite powders, amorphous metal powders or coated particles with optional thermoset polymers. The amorphous metal powders are described in copending and coassigned U.S. patent application Ser. No. 071,800,632, U.S. Pat. No. 5,278,377. The coated particles can be particles, such as glass fibers, glass bubbles, or mica flakes, coated with a thin, continuous metallic film. Such coated particles are described in copending and coassigned U.S. patent application Ser. No. 071,668,974, U.S. Pat. No. 5,529,708. Most kinds of thermoplastic polymer can be bonded by this method. Preferably, the method employs a thermoplastic polymer as described in the present application.

The invention is also directed to a method for bonding two components. The method includes the steps of coating at least a portion of one or both of the components with a thermoset adhesive mixed with susceptor particles wherein that portion is an area of the component to be bonded to the other component. The areas of the components to be bonded together are contacted. Those contacted areas are irradiated with electromagnetic radiation. The susceptor particles absorb the radiation and enhance green strength of the adhesive. Conveniently, the components may be a tube and a fluid transporting part.

The invention is also directed to a composition of matter, comprising a mixture of a thermoset adhesive and susceptor particles. Conveniently the thermoset adhesive is an epoxy adhesive, and the susceptor particles are for example particles coated with ferromagnetic or ferromagnetic material, particles coated with conductive material, and ferromagnetic amorphous powders. The volume loading of the susceptor particles in the mixture is preferably between about 1% and about 65%, and more preferably between about 1% and about 30%.

The multilayered film and film based medical device assembly of the present invention are flexible, tough, abrasion resistant and heat formable. They do not release harmful chemicals such as hydrogen chloride to the atmosphere when they are burned or otherwise degraded. The multilayered film and film based assembly of the present invention are also safe and effective for use in medical applications. At least the surface layers of the film and assembly contain no plasticizer or other leachable or extrudable ingredient which could contaminate pharmaceutical fluids. In particular, at least the surface layers contain no phthalate or citrate esters or other plasticizers or additives which are capable of leaching into pharmaceutical fluids. The multilayered film and film based assembly also have an ability to avoid absorption of solvents, drugs, pharmaceutical agents and other materials which come in contact with the film and film based assembly. This characteristic is especially desirable when the film and film based assembly are used as medical products. In this application, the film and film based assembly display minimal or no absorption of drug, pharmaceutical carrier or other pharmaceutical liquid. Optionally, the film and film based assembly layers can be composed of thermoplastic polymers which will make the layers resistant to acid, solvent, UV light, and will render the film and film based assembly clear or opaque or colored.

DETAILED DESCRIPTION OF THE INVENTION

Figure 1:
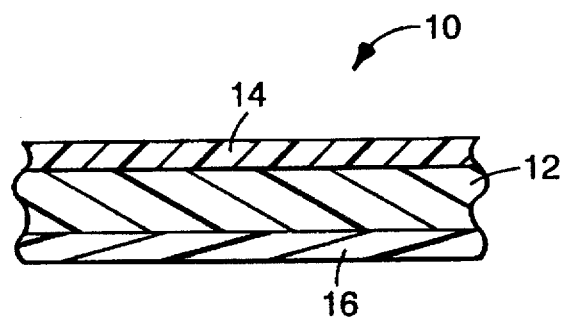
FIG. 1 is a cross-sectional view of a first embodiment of a multilayered film assembly having outside and inside surface layers and a core layer.

The multilayered film and film based assembly of the present invention possess physical characteristics much like those of polyvinyl chloride (PVC) film and film based assemblies. In addition, the multilayered film and film based assembly are environmentally safe and avoid medical, pharmaceutical and health-related drawbacks of PVC. The polymeric layers of the multilayered film and film based assembly are made of a core layer of at least one soft, flexible thermoplastic polymer and surface layers of at least one tough, abrasion-resistant thermoplastic polymer. These layers contribute a composite of their characteristics to the multilayered film and film based assembly. Moreover, the core layer is preferably at least slightly larger in thickness than either of the two surface layers. In this fashion the flexibility characteristics of the core layer dominate the composite. At least the surface layers and preferably all layers are free of any additives, plasticizers or other components which could be extracted or could exude or leach into fluids in contact with the layers.

DEFINITIONS

Certain terms and phrases are used to describe the film and film based assembly. Generally, these terms and phrases have the ordinary definitions understood by those of skill in the art. Several, however, have particular meanings as given below.

The term "Young's modulus" means the amount of force per unit volume of material needed to elongate the material a unit distance after the stress has been initiated and before the curve of stress against elongation becomes non-linear. The Young's modulus is measured in megaPascals (MPa).

The term "cassette" means a device generally formed of a multiple number of overlaid plastic sheets. The cassette possesses internal passages and/or chambers and/or bubbles suitable for conducting fluids. The cassette may be a pumping cassette suitable for metering fluids in connection with an infusion pump.

The term "plastic fluid transporting component" means a component formed at least partially of a polymer and having a lumen for conducting fluid. Non-limiting examples include cassettes, tubing, luer locks, injection sites, bag spikes, filters, check valves, and drip chambers.

The term "environmentally compatible" means capable of being handled or treated by a usual method for disposal of medical devices without the release of harmful, noxious or toxic substances to the environment. Usual methods for such disposal include but are not limited to burning and burying.

PHYSICAL CHARACTERISTICS

Toughness and resistance toward abrasion and cuts as well as high flexibility are physical characteristics that are essential for medical film and film based medical device assemblies. The medical film and film based assembly must survive the long term abrasion forces of such medical instruments as infusion pumps and friction fittings. They also must have high flexibility and elasticity so that internal fluid channels and pumping bubbles will maintain their integrity and operate under repetitive flex conditions.

Tough, abrasion resistant thermoplastic polymers typically are not flexible enough for use in medical films and film based assemblies. Highly flexible thermoplastic polymers typically are not tough enough for use in medical films and film based assemblies. Consequently, until the present invention, a non-PVC film had not been developed which exhibited a toughness, abrasion resistance, flexibility, durability, non-stick release, flexibility and expansion without failure.

According to the present invention, a multilayered film of a flexible chlorine-free thermoplastic polymer core layer and tough, thermoplastic polymer outside and inside surface layers, and a film based medical device assembly of at least two overlapping, heat and compression joined films have been made which have flexibility, durability, elasticity, strength, toughness, abrasion resistance, non-stick release and expansion without failure. The multilayered film and film based assembly incorporate at least the following parameters a through e and preferably the remaining parameters as well.

a. The first thermoplastic polymer has a flexibility mimicking or greater than that of polyvinyl chloride medical film. More specifically, the first thermoplastic polymer has a flexibility sufficient to enable the film to endure mechanical pump action on an expanded bubble formed from the film; i.e. flexing from a fluid filled, fully expanded bubble, down to a completely flat, unfilled condition where the pumping occurs repeatedly between two hard surfaces. Preferably the flexibility of the first thermoplastic polymer is measured by its Young's modulus which in especially preferred embodiments is within a range of about 15 to about 40 MPa (megaPascals). Examples of PVC medical films acting as reference points for the flexibility mimicked by the first thermoplastic polymer include but are not limited to medical and general purpose PVC films such as PVC film plasticized with 40% diethylhexyl phthalate manufactured by O'Sullivan Corporation of Newton Upper Falls, Mass. Also illustrative of PVC properties in medical applications include "Nalgene" brand USP VI grade tubing, commercially available from Nalge Co. of Rochester, N.Y., and "Tygon" brand tubing commercially available from Norton Performance Plastics of Wayne, N.J. The Young's modulus of the PVC's used in such films range from about 17 MPa to about 40 MPa.

b. The second thermoplastic polymer and preferably but not necessarily the third thermoplastic polymer have a Young's modulus that is not more than about ten times, preferably from about equal to, up to no greater than, about ten times, more preferably within a range of greater than, up to about ten times, the Young's modulus of the first thermoplastic polymer. Especially preferably, the Young's modulus of the second thermoplastic polymer ranges up to no more than about seven times, most preferably up to no more than about three times, the Young's modulus of the first thermoplastic polymer. Preferred embodiments have a Young's modulus of the second thermoplastic polymer within a range of from about 15 to 300 MPa, more preferably within a range of from about 15 to 150 MPa.

c. The core of the film provides at least a slight majority of the film thickness relative to any other single layer. More specifically, the thickness ratio of the film layers incorporating first thermoplastic polymer to the film layers incorporating second, third and additional thermoplastic polymer is about 1:1 to about 10:1, preferably from about 1:1 to about 5:1. This parameter allows the flexibility of the film core to dominate the composite flexibility characteristics of the multilayered film.

d. The multilayered film through the action of the third thermoplastic polymer and the third thermoplastic polymer itself have a capacity to self-heat seal before the core and the outside surface layer become plastic or otherwise deform under heat. Further, the film is capable of being expanded through pressure molding to form expanded structures within the film such as pockets which can repeatedly be compressed over a long duration without failure. The expansion also is achieved without failure of film integrity, flexibility and resilience.

e. The outside surface layer of the film and in preferred embodiments, the multilayered film based assembly itself preferably exhibit a hot surface release and an abrasion resistance that mimic or are greater than that of polyvinyl chloride medical film. More specifically, the outside surface layer of the film, and preferably, the multilayered film itself, exhibits an outside surface abrasion resistance having an abrasive index range of at least about 100 as measured by ASTM test D1630-83, the standard test method for rubber property-abrasion resistance.

f. In addition to the flexibility of the first thermoplastic polymer and the core of the film, the multilayered film itself preferably exhibits a flexibility that mimics or is greater than that of polyvinyl chloride medical film. More preferably, the multilayered film has a Young's modulus within a range of about 15 to about 60 MPa.

g. The multilayered film preferably exhibits essentially complete resiliency in an expanded form and essentially no expanded wall failure during an endurance test as a rolling diaphragm of at least 10,000 cycles through expansion and compression between a completely filled condition and a completely collapsed condition. The wall should return to its original state to show essentially complete resiliency. It should not crack or exhibit signs of stress weakening to show essentially no wall failure.

The multilayered film and film based assembly are capable of bonding to themselves and to other plastics through the use of adhesive bonding, radio frequency welding, microwave welding and thermal welding. The multilayered film and film based assembly are sterilizable through gamma irradiation and ethylene oxide. They preferably do not degrade under such sterilizing conditions. The multilayered film and film based assembly resist oxidative and ultraviolet degradation such that in a preferred embodiment, they have a significantly long shelf life and do not turn yellow or age like polyvinyl chloride.

Core Layer Thermoplastic Polymer

The first thermoplastic polymer is used to form the core layer of the film. It includes any soft conformable thermoplastic polymer having the characteristics, flexibility and preferably the Young's modulus as described above. Preferred thermoplastics include polymers of a C2 to C4 mono-unsaturated alkene, copolymers of a majority of a C2 to C4 mono-unsaturated alkene with a minority of a substituted olefin monomer such as C4 to C14 mono-unsaturated alkene or a C8 to C14 aryl alkene, and copolymers of a majority of a C2 to C4 mono-unsaturated alkene with a minority of a substituted C2 to C6 mono-unsaturated alkene having a substituent such as C1 to C6 alkoxy carbonyl, carboxylic acid, carboxamide and carboxylic ester groups. Examples include copolymers of olefins such as ethylene and propylene with substituted olefins such as vinyl acetate (EVA or PVA), N-methyl acrylamide (EAM or PAM), acrylic acid (EAA or PAA), methacrylic acid (EMA and PMA), EMA or PMA ionomers (EMAZ, EMAS or PHAZ with metals such as zinc or sodium) and acrylate and methacrylic esters having C1 to C6 alkyl groups. In the case of EVA and PVA, the acetate can be partially or wholly hydrolyzed to yield poly(vinyl alcohol) (PEA). Examples as well include ethylene or propylene copolymers of all hydrocarbon substituted olefins such as ethylene or propylene and styrene (ES or PS), ethylene or propylene and butene (EB or PB) and ethylene or propylene and octene (EO or PO). Particular examples include copolymers of ethylene and vinyl acetate, ethylene and butene, ethylene and n-butyl acrylate, and ethylene and ethyl acrylate.

Generally, as the amount of substituted olefin monomer or alkyl or aryl olefin monomer is increased in such an olefin copolymer, the Young's modulus of the copolymer will decrease. Consequently, the ratio of majority olefin monomer to minority substituted olefin monomer in the copolymer will be selected so that the copolymer will have the appropriate Young's modulus as described above. Preferably, this amount is from about 2% to about 50%, especially preferably about 10% to about 40% on a molar basis.

Under certain circumstances, the first thermoplastic polymer can also have characteristics suitable for one of the surface layers. Film constructions of this nature will at least be tri/bilayer film where the core layer is also acting as one of the surface layers.

Outside and Inside Surface Layer Thermoplastic Polymers

The second and third thermoplastic polymers include any tough, abrasion resistant thermoplastic polymer having the characteristics and the high Young's modulus as described above (especially, the important distinctive characteristics of non-stick release and self-sealing, respectively). In addition to linear backbone structures providing a high order of intermolecular orientation, other desirable backbone structures for the second and third thermoplastic polymers include those having: cross-linking, backbone branching, grafting, ionomeric linking, a combination of crystalline and amorphous domains, hydrogen bonding and molecular orientation such as through a backbone structure that restricts the degrees of three dimensional movement of the backbone (hereinafter, Intermolecular Linking). Generally the second and third thermoplastic polymers have the same characteristics but are not necessarily of the same chemical structure. Preferably, the second and third thermoplastic polymers include polyolefins, cross-linked polyolefins, olefin-substituted olefin copolymers as well as polyurethanes, polyethers, and polyesters. The olefinic monomers used alone or in combination to form the polyolefins can be selected from aliphatic and aromatic olefins of two to fourteen carbons such as ethylene, propylene, butene, octene and styrene. Preferred polymers and copolymers of such olefins include polyethylene, polypropylene, copolymers of ethylene and butene (EB) and copolymers of ethylene and styrene (ES). In copolymers of olefins, the minor olefin monomer (C4 to C14) preferably is present in a range of from about 1% to about 20% on a molar basis.

When a copolymer of a C2 to C4 olefin and a substituted olefin is used as a second or third thermoplastic polymer, the substituted olefinic monomers can also be selected from C2 to C4 mono-unsaturated olefins with such substituents as acetoxy, oxyalkanoyl, carboxyl, carboxamido and other similar polar groups. Examples include acrylic acid, methacrylic acid, acrylamide and similar hydrogen bonding or cross-linkable olefins.

The optional Intermolecular Linking in the second and third thermoplastic polymers will be low enough to preserve the thermoplastic character of the polymer but sufficient to provide the degree of abrasion resistance and toughness meeting the Young's modulus requirement described above. Preferably the Intermolecular Linking is in the range of from about 0.1% to about 10% especially preferably about 0.2 to about 5% on a molar basis. Moreover, as indicated above, the thermoplastic olefin copolymers are selected according to the guidelines affecting the Young's modulus. Preferred copolymers include a majority of C2 to C4 olefin monomer and a minority of polar, aprotic substituted olefin monomer. Preferably, the amount of minority monomer present is from about 2% to about 40%, preferably about 5% to about 30% on a molar basis.

Preferred Polymers for Core and Surface Layers

In preferred embodiments, the first, second and third chlorine-free thermoplastic polymers are all olefinic polymers. Examples of preferred first thermoplastic olefinic polymers include ethylene-vinyl acetate copolymers (EVA), ethylene-methyl acrylate copolymers (EMAC), ethylene alkyl acrylate copolymers such as ethylene n-butyl acrylate copolymers (EBA), ethylene-butene copolymers (EB), and combinations thereof. Other examples include the foregoing blended with ionomers.

Nonlimiting examples of second thermoplastic olefinic polymers include ethylene-octene copolymers (EO) (such as the Attane™ copolymers manufactured by Dow Chemical Co., Midland, Mich.), EMAC copolymers (such as are manufactured by Chevron Chemical Corp., of Houston, Tex.).

Nonlimiting examples of the third thermoplastic olefinic polymers include ionomeric ethylene-methacrylic acid copolymer with zinc (EMAZ) or sodium (EMAS) doping, such as the Surlyn™ copolymers manufactured by the DuPont Co., Wilmington, Del.

The first, second and third thermoplastic polymers may also constitute olefin copolymers of the same two monomers but with differing ratios of those monomers. That differing ratio changes the modulus value of the resulting copolymer and hence makes the copolymer a first, second and third thermoplastic polymer. For example, the first, second and third thermoplastic polymers can all be obtained from EVA and EBA copolymers by altering the percent by weight content of vinyl acetate (VA) and n-butyl acrylate (n-BA)

monomers, respectively, in those EVA and EBA copolymers. EVA and EBA copolymers with relatively high VA and n-BA contents provide low Young's modulus materials suitable for use in the core layer of multilayered film. On the other hand, EVA and EBA copolymers with relatively low VA and n-BA contents provide high Young's modulus materials suitable for use in the outside surface layer and the inside surface layer. For example, when an EBA copolymer composes the outside and inside surface layers, its n-BA content is preferably from about 1% to about 20%, more preferably from about 1% to about 15%, and most preferably from about 2% to about 10% on a molar basis. In another example the core layer of a three layer film is an EVA copolymer with a VA content of from about 20% to about 30% VA, while the outside and inside surface layers are EVA copolymer with a VA content of from about 5% to about 10% VA on a molar basis. Alternatively, the outside surface layer of that film can be an EVA copolymer with a VA content of from about 5% to about 10% VA, while the inside surface layer of that film can be an EVA copolymer with a VA content of from about 10% to about 20% percent VA on a molar basis.

Dimensions

The thicknesses of the core and surface layers and of multilayered film and film based assembly will vary depending upon the intended use, and thus, can readily be selected by those skilled in the art. However, in a preferred embodiment, the outside and inside surface layers are moderately thin layers covering the core layer. In particular, the increased hardness and toughness of the outer surface layers, and the heat seal requirements of the inner layer, allow them to be coextruded as thinner layers than the core. In particular, these layers function to protect the core from abrasion and pick-up of dirt, serve as a release layer (outside surface) to assist in removing a molded assembly from a mold, and serve as a self-sealing layer (inside surface). Accordingly, the ratio of the thickness of the two surface layers to the core layer is preferably from about 1:1 to about 1:14, more preferably from about 1:2 to about 1:14. For example, when using the preferred EVA, EO, and EMAZ or EMAS copolymers to form a film and film based assembly according to the present invention, a core layer is preferably from about 125µ to about 350µ, more preferably from about 200µ to about 300µ, and most preferably from about 200µ to about 275µ thick, while the outside and inside surface layers are each preferably from about 25µ to about 125µ, more preferably from about 50µ to about 100µ.

Thermoplastic Polymer Modulus Measurement

The stiffness/flexibility of a given thermoplastic polymer is conveniently measured and expressed in terms of the Young's modulus, as reported in megaPascals (MPa), for the polymer. A polymer with a low Young's modulus (e.g., from about 6 MPa to about 30 MPa) is soft and flexible while a polymer with higher Young's modulus values (e.g., from about 25 MPa to about 300 MPa) is relatively stiff and inflexible. The low Young's modulus polymers also tend to be more easily cut or physically abraded and serve as the first thermoplastic polymer. Conversely, the high Young's modulus polymers present a relatively hard, tough (i.e., cut and scratch-resistant) surface and serve as the second thermoplastic polymers.

The following examples section provides the details for such measurements as applied to multilayered films. The functional and numeric parameters for stiffness and flexibility of the first, second and third thermoplastic polymers used in the multilayered films are related to, and in preferred embodiments, are indicated by the Young's modulus of these polymers. Those parameters are given above.

The measurement of Young's modulus was performed using a Material Test System (MTS) 880 (MTS Systems Corporation, Eden Prairie, Minn.) with an MTS Sintech Testworks II Application Software Package, version 2.1. Samples of film were prepared for testing by cutting strips 0.5 inch (1.2 cm) wide by 6 inches (15.24 cm) long. These were then inserted into the gripping jaws of the MTS testing machine, and a rate of elongation of 15.24 cm (6 inches) per minute was set. For each film sample, three replicates were run. For each replicate the following information was computed and averaged:

1. Young's modulus, computed as the maximum slope of the stress/strain curve, using a 3% strain segment length (actually the slope at 0% strain).
2. Load at 50% strain
3. Stress at 50% strain Since stress/strain characteristics can change over time after extrusion, measurements are reported after at least one month following extrusion unless otherwise stated.

Tie Layer and Optional Additives

While it is preferable not to utilize a tie layer or layers in the multilayered film to bond the various layers together, there may be multilayered constructions in which such layers are desired. When a tie layer is employed, it can be composed of materials which provide structural integrity to the multilayered constructions, without substantially affecting the other desirable characteristics of the multilayered film, such as flexibility, clarity and environmental-compatibility. The selection of the particular tie layer material to be utilized in multilayered film according to the present invention, from the wide variety of available tie layer materials, is subject to the particular needs and preferences of those skilled in the art. Preferred tie layer polymers include viscoelastic polymers which have functionalities that are compatible with and bind to the layers to be tied, which in the case of preferred embodiments may be copolymers of methacrylic acids.

To provide specific additional characteristics to multilayered films of the present invention, any one, or all, of the layers can also contain conventional non-leachable additives, such as antistatic materials, pigments, dyes, UV absorbers, nucleating agents, quenching agents and the like. For example, ultraviolet absorbers can be added to one or more of the layers of the multilayered film for application in IV cassettes used with light-sensitive drugs.

Methods of Preparation

The preferred method of preparing multilayered film and film based assembly according to the present invention is through coextrusion. Coextrusion is a polymer processing method for bringing diverse polymeric materials together to form a unitary layered structure, such as film and sheets of the film. This allows for unique combinations of materials, and for structures with multiple functions, such as, toughness, flexibility and environmental compatibility.

Component polymeric materials according to present invention can be coextruded from the melt state in any shape, according to the intended end use thereof. The shape and/or thickness of the coextruded layers will be dependent upon the efficiency of the particular extrusion equipment utilized. Generally, films having a flat continuous sheet construction are the preferred coextruded structures. The films can be formed by coextrusion from linear dies and optional hot calandaring and by coextrusion from circular dies followed by gas pressure expansion. Where appropriate, the multilayered film and film based assembly according to the present invention can be uniaxially, biaxially or multi-axially oriented to further enhance its physical characteristics.

For example, in a preferred construction, a multilayered film according to the present invention is composed of a coextruded cast film of a core layer of an EVA coplymer with a VA content of about 28%, an outside surface layer of an EO copolymer (e.g., an EO such as the Attane™ copolymer manufactured by the Dow Chemical Co., Midland, Mich.)

and an inside surface layer of an ethylene-methacrylic acid, zinc or sodium ionomeric copolymer (e.g., an EMAZ or EMAS such as the Surlyn™ copolymer manufactured by DuPont Co., Wilmington, Del.). A three layered film can be coextruded with the foregoing technique wherein the outside surface layer is the EO copolymer and the inside surface layer is the EMAZ or EMAS copolymer. Also, a five-layered film in which the outside surface and divider layers are composed of an Attane™ copolymer is preferred.

The method for forming a film based assembly includes several steps. The first involves forming a film as a sheet material by coextruding the first, second, third and optional divider thermoplastic polymers as contiguous united layers. In a second step, the molded portion of the assembly is produced by heat bonding two of the sheets in a compression blow mold having at least two mold halves with at least one having internal cavities. Two sheets of the film are placed between the mold halves with their outside surface layers facing the mold halves and their inside surface layers positioned to touch each other when the mold is closed. The molded portion of the assembly is molded by closing the mold halves and applying pressure and heat to the sheets while applying gas pressure to the portions of the sheets within the internal cavities. The self bonding core layers or inside surface layers of the sheet films bond to each other and the portions of the sheet films within the mold cavities expand to form the desired internal structure of the molded portion of the assembly.

The molded portion of the assembly is then bonded to its connective or other preformed parts, which usually is polymeric tubing. In preferred embodiments, the polymeric tubing will also be fabricated from chlorine-free polymers as described in copending U.S. patent application Ser. No. 08/103,328 U.S. Pat. No. 5,562,127, filed on even date with this application and entitled "Multilayered Tubing", the disclosure of which is incorporated herein by reference. This bonding may be done by appropriate adhesives, or may advantageously be performed by applying a mixture of a polymeric binder and susceptor particles to the apparatus, placing parts of the apparatus, in contact with each other, and subjecting the combination to electromagnetic radiation. The susceptor particles absorb electromagnetic energy and generate heat. This heats the polymeric binder material and heat welds the components together. Additional information about the preferred susceptor bonding technique is described in coassigned U.S. patent applications Ser. No. 07/588,591 U.S. Pat. No. 5,294,763, Ser. No. 07/668,974 U.S. Pat. No. 5,132,776, and Ser. No. 07/800,632 U.S. Pat. No. 5,278,377, the disclosures of which is incorporated herein by reference.

Preferred Embodiments

Figure 2:
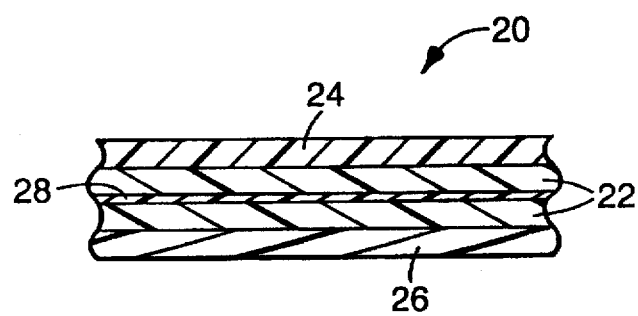
FIG. 2 is a cross-sectional view of a second embodiment of a multilayered film having outside and inside surface layers, a core layer of two parts and a divider layer between the two parts of the core layer.
Figure 3A:
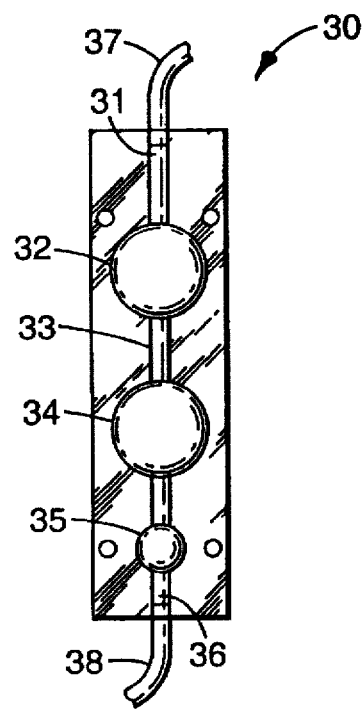
FIGS. 3A and 3B are top and left side views respectively of an embodiment of a film based assembly according to the invention. The embodiment is a medical pump cassette.
Figure 3B:
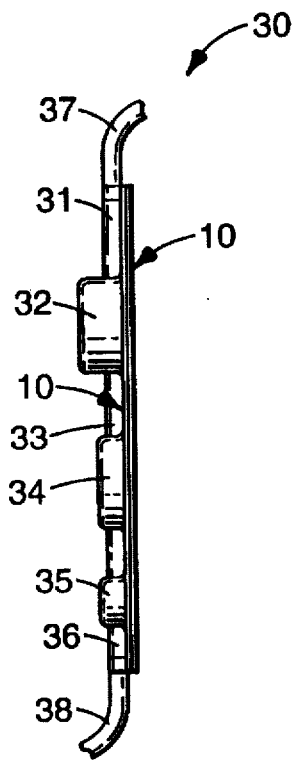

FIGS. 1 and 2 show cross-sectional illustrations of two alternative embodiments of the multilayered films 10 and 20 while FIGS. 3A and 3B show top and left side views of a cassette 30 according to the present invention. FIG. 1 shows a first embodiment in which multilayered film 10 having a core layer 12 of a first, chlorine-free, soft, flexible thermoplastic polymer contacting an outside surface layer 14 of a second chlorine-free, tough, durable thermoplastic polymer and an inside surface layer 16 of a third chlorine-free, self-bonding thermoplastic polymer. The first thermoplastic polymer is substantially softer than the second and third thermoplastic polymers. The surface layers 14 and 16 provide tough, protective coatings for the softer, core layer 12. The Young's modulus of the first thermoplastic polymer is less than to within about 250% of that of polyvinyl chloride used in flexible elastomeric medical applications, preferably in the range of about 15 to about 50 MPa (megaPascals). The Young's modulus of the second and third thermoplastic polymers is higher than but not more than about seven, preferably three times the Young's modulus of the first thermoplastic polymer, preferably in the range of about 15 to about 150 MPa.

In a particularly preferred embodiment, the core layer of the multilayered film is composed of EVA copolymer and/or (ethylene-butylene) EB copolymer known as Exact™ manufactured by Exxon Corp. Floral Park, N.J. For example, the core layer of the multilayered film 10 (FIG. 1) can be about 200μ to 325μ of an EVA copolymer with about a 20–30% VA content or an EB copolymer, while surface layers 14 and 16 respectively can be 50 to 75μ of an EO copolymer such as an Attane™ copolymer manufactured by Dow Chemical Co. of Midland, Mich. and 25 to 100μ of an EMAZ copolymer such as a Surlyn™ copolymer manufactured by DuPont Co., Wilmington, Del. No adhesive layer is required to adhere the core and surface layers 12, 14 and 16 of this multilayered film 10 together. Instead, upon hot-melt coextrusion, the core and surface layers readily adhere to one another to form an integrated three-layered structure. However, if need be, it is also within the scope of the present invention to use an additional material, such as an adhesive, to adhere the core and surface layers and of multilayered film and film based assembly together.

FIG. 2 shows a second embodiment of multilayered film and film based assembly 20 according to the present invention. As with the embodiment illustrated in FIG. 1, this embodiment includes core layer 22 of a first, chlorine-free, soft flexible thermoplastic polymer contacting outside surface layer 24 of a second, chlorine-free, tough, durable thermoplastic polymer and inside surface layer 26 of the third chlorine-free polymer. In addition, this embodiment contains a divider layer 28 in the approximate middle of the core layer 22. The divider layer is composed of the second thermoplastic polymer and acts to increase the stabilization of the core layer during film and film based assembly formation. This embodiment is especially preferred for use in construction of a film based assembly in which precision of the molded internal structures is desirable.

FIGS. 3A and 3B show a medical pump cassette embodiment of the film based assembly. The medical pump cassette is configured and operates according to disclosure provided by U.S. Pat. No. 4,236,880, the disclosure of which is incorporated herein by reference. Sheet films 10 and 20 formed preferably as depicted in FIG. 2 constitute the work piece for the molded component. Sheet film 10 is bonded to sheet film 20. Sheet film 10 contains molded tubes 31 and 36 which form the inlet and outlet of the molded component. Tube 31 connects to bubble 32 which is the first piston pumping reservoir for the cassette. Bubble 32 is interconnected to bubble 34 by interconnecting molded tube 33. Bubble 32 is the second piston pumping reservoir and connects to outlet molded tube 36. Medical fluid polymeric tubing 37 and 38 is respectively bonded to molded tubes 31 and 36 to complete the assembly.

The infusion pump cassette 30 has a low level of undesirable extractables. This cassette has a form and function similar to an existing infusion therapy cassette presently sold by 3M (FIG. 3A). This cassette is the metering element of a complete disposable infusion therapy set which includes tubing, luer locks, spike, drip chamber, clamps, etc. In use, it is inserted into a mechanical metering pump. It meets high performance requirements, including those in Table 5 of Example 5 below.

The cassette of this invention is made from a multilayer polymeric film 10, 20 replacing plasticized PVC. This film can be three layers (FIG. 1) or more (FIG. 2) layers, with individual layers composed of single or blended polymers. The composite film construction 10, 20 must have a modulus low enough (for Example, 15 to 50 MPa) to produce fluid chambers that will pump and roll-back reproducibly, a surface on one side that is capable of forming a strong heat seal to at least like materials, and a surface on the other that will release from thermoforming molds and/or heat-sealing plates, and serve as an outside protective layer for the finished cassette. The composite film 10, 20 has sufficient dimensional stability during the thermoforming and heat seal process of forming the cassette, that a minimum of internal distortion is built into the cassette's internal fluid paths and pumping chambers. The film 10, 20 is also optically clear to allow nurses to see and remove air bubbles during priming.

Figure 4:
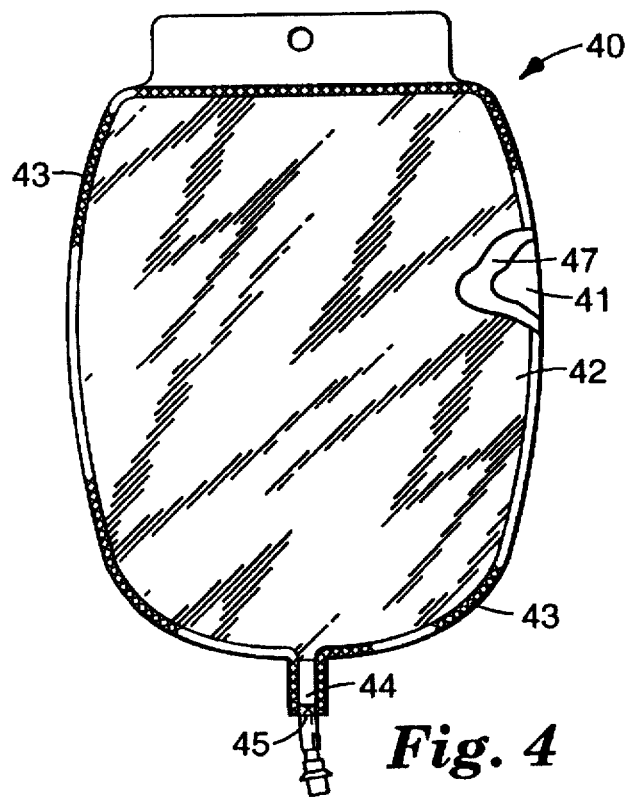
FIG. 4 is a medical IV bag compression mold formed from two sheet films according to the present invention.

FIG. 4 shows a medical IV bag 40 which is compression mold formed from two sheet films according to the invention. The sheet films are trilayer construction in which the inside surface layer 41 forms the inside surface of the bag while outside surface layer 42 forms the outside surface of the bag. Core layer 47 and layers 41 and 42 are coextruded such that they are continuously united. Heat seal 43 along the outside perimeter of bag 40 is caused by self bonding of core layer 41. Needle spike access 44 is epoxy welded to outlet duct 45 formed in the top 46 of bag 40 by jointly forming the heat seal 43, duct 45 and epoxy welding of access 44.

Figure 5:
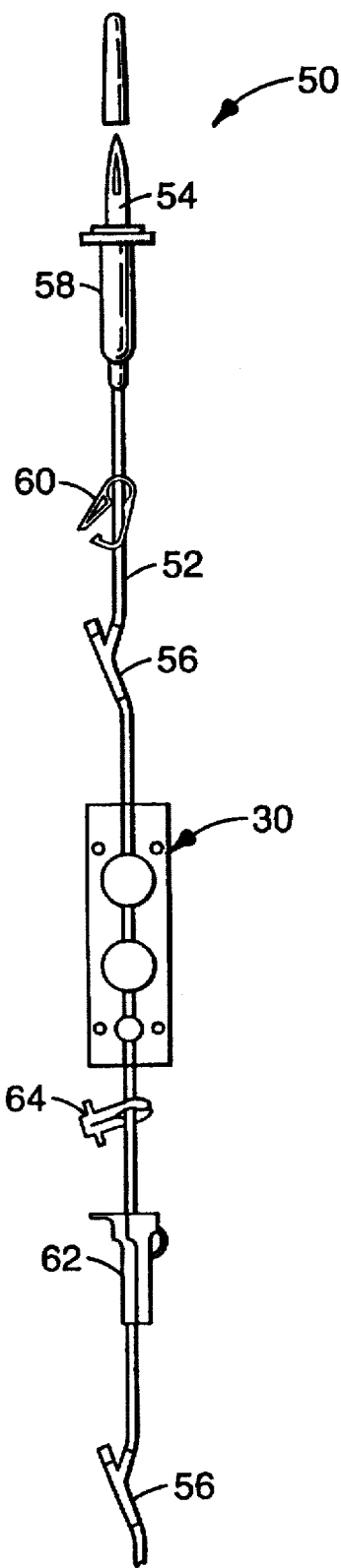
FIG. 5 is a complete medical IV tubing assembly.

FIG. 5 shows a complete medical IV tubing assembly 50, including a cassette 30 as described above in connection with FIGS. 3A and 3B. In preferred embodiments, the other elements which comprise the medical IV tubing assembly 50 will themselves be free of polyvinyl chloride in their composition. Tubing 52 is provided as a plastic fluid transporting component, preferably its composition is a composite material such as that discussed in copending and coassigned U.S. patent application Ser. No. 08/103,328, U.S. Pat. No. 5,562,127, cited above. Such conventional elements as the bag spike 54 and the Y-sites 56 may be conveniently made from stiff thermoplastic materials; polycarbonate or ABS (acrylonitrile-butadiene-styrene) polymer, are considered particularly suitable. The drip chamber 58 requires optical clarity for its function, and e.g., polypropylene, polycarbonate or acrylic polymers may be used. Pinch clamps 60 and roller clamps 62 may be provided, and these are conveniently made from high density polyethylene. A slide clamp 64 may be provided, conveniently made from stainless steel.

Susceptor Particle Bonding

A method for susceptible particle bonding of plastic articles is also contemplated by the invention. As described above, two thermoplastic articles can be heat sealed together through the use of susceptor particles coated at the bonding joint. The susceptor particles absorb electromagnetic radiation and convert it to heat. The heat in turn causes the heat sealing of the thermoplastic articles. These methods have been described in U.S. application Ser. No. 07/588,591, U.S. Pat. No. 5,294,763 U.S. patent application Ser. No. 07/668, 974, U.S. Pat. No. 5,529,708 and U.S. application Ser. No. 07/800,632, U.S. Pat. No. 5,278,377 the disclosures of which are incorporated herein by reference. The general methods for forming such a plastic article bond are described in these applications. Generally, the method involves forming an interlayer of the susceptor particles between the two portions of the plastic articles which are to be bonded together as a joint. The joint is then exposed to electromagnetic radiation to cause heat sealing.

For the purposes of the present invention, the susceptor bonding technology for assembling the components of the sets provides advantages over adhesives. The susceptor particles themselves can be made with very little metal content, and those metals can be chosen to be biologically and environmentally compatible. By proper choice of the polymeric binder, most thermoplastics can be joined together. Typically, the polymeric binder is comprised of the same materials that the components to be joined are comprised. Susceptor technology allows one to heat only the bond area of the assembly, the rest of the assembly need not be subjected to heat. Conventional adhesives, such as cyanoacrylates, one or two part epoxies or UV cure epoxies can contain reactive materials that are not medically suitable, can not bond all materials such as polypropylene or polyethylene, and may require heating of the entire assembly to cause or speed the cure of the adhesive.

Utility of the Invention

Multilayered film and film based assembly according to the present invention can be utilized in a wide range of both medical and nonmedical products. In the medical area the multilayer film and film based assembly is suitable for replacing chlorine-containing PVC film and film based assembly, such as is utilized with intravenous (IV) fluid administration sets, infusion sets, cassettes, blood bags, IV fluid bags, arthroscopy fluid control systems, cardiovascular systems and blood gas monitoring systems. UV absorbers can be added to one or more of the layers of multilayered film and film based assembly for application in IV sets used with light-sensitive drugs. This adaptation of the multilayer film and film based assembly will not absorb drug or medical fluids and will not contaminate the drug or medical fluid with additive, plasticizer and the like through extraction or leaching.

These and various other advantages and features of the invention are pointed out broadly by the foregoing general specification. The following examples are provided to further illustrate the invention. These examples are not meant to limit the broad scope of the invention, however.

EXAMPLE 1

An EVA Core Trilayer Film

A 375μ trilayer film was co-extruded from three polymers: a top layer consisting of a 50μ layer of an ultra low density co-polymer of ethylene and octene (Dow Attane™ 4602), a 275μ core layer of a soft EVA (28% VA) (Quantum UE-645-04), and an inside, heat seal layer consisting of a 50μ layer of an ionomer resin that is a co-polymer of ethylene and methacrylic acid doped with zinc (Dupont Surlyn™ 1702). A 20 cm wide three manifold adjustable vane die was used. The Attane™ 4602 was fed to one of the outside manifolds of the die by a 2.5 cm Killion™ single screw extruder using a conventional screw (Killion, Inc., Verona, N.J.); the Surlyn™ was fed to the other outside manifold by a similar extruder; the EVA core was supplied to the middle chamber from a 30 mm co-rotating twin screw extruder compounder (37:1 L/D) with a Zenith pump for metering.

The temperature profiles for these three extruders is given in Table 1. (Unless otherwise indicated the extruder conditions for film formation according to each Example are given in Table 1.) The co-extruded film was cast onto a 30 cm diameter chrome roll held at a temperature of 12° C., and then immediately passed through a nip between this chrome roll and a rubber roll.

Figure 6:
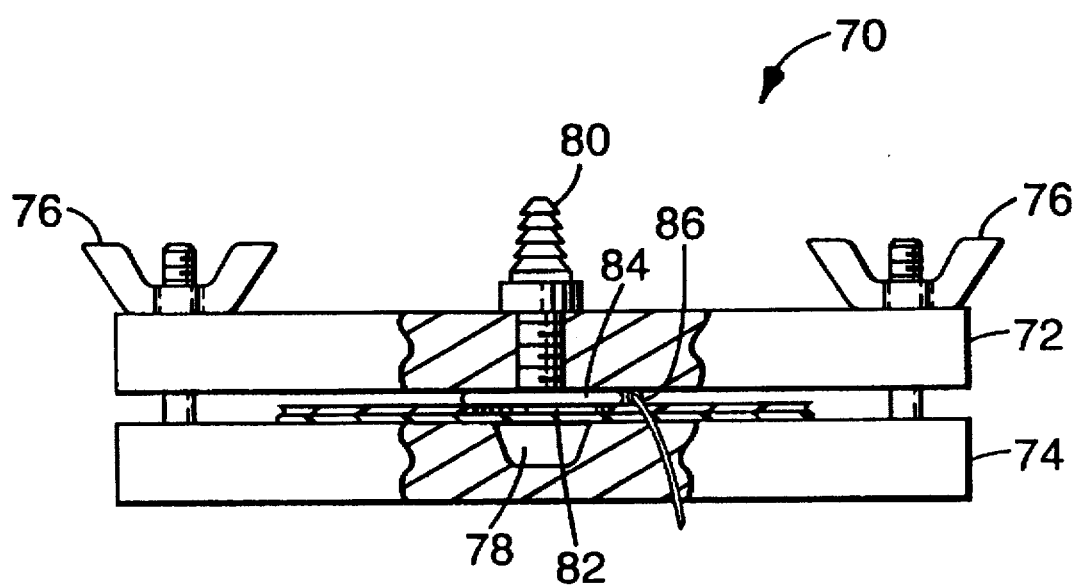
FIG. 6 is a view of a cassette forming device.

To estimate the best cassette forming conditions for this film, a simple laboratory-scale forming device was used. This device (shown in FIG. 6) consists of two aluminum blocks that can be held together by wing nuts. The lower block has a small cylindrical hole, or well, into which the film can be thermoformed when heat and air pressure is applied. The top block was fitted with an air pressure connection. The film layers were placed in the former (centered over the cylindrical hole), with the Surlyn™ copolymer sides facing one another, and the Attane™ copolymer sides facing the aluminum blocks. A hole had been cut in the upper film layer to allow pressurized air to get between layers. An O-ring was placed over the film sandwich, centered over the hole in the film and the hole in the lower block. A thermocouple was placed between the film layers, and positioned adjacent to the O-ring. The top block was then placed down over the O-ring and film assembly and tightened down by wing nuts. This formed a pressure seal around the sample above the deflection well. The air inlet port of the device was connected to compressed air. The air pressure was adjusted to 3 psi (0.2 kg/cm$^2$) using an in-line gauge. This assembly was then put into a Despatch oven set at 121° C. and heated until the thermocouple read 93° C. (18 minutes). The whole assembly was then immediately immersed in room temperature water to quench the construction.

This experiment was repeated several times, each time with a higher final ("formation") temperature. The details are summarized in Table 2.

Complete chamber formation at 106° C. and 116° C. means the film completely filled the well and took its shape. Partial formation typically means the film formed domes which were smaller than the well. The heat seal between the layers occurred under the O-ring, taking essentially the shape of the O-ring. At 106° C. and 116° C., the seal between the layers was strong. When an attempt was made to pull the two halves of these films apart at the heat seal, the film itself tore and appeared to separate internally, rather than within the seal itself. The film released readily from the aluminum mold halves. In subsequent experiments, a heat gun was used to heat the assembly. Using the heat gun, samples could be heated to 107° C. within 5 minutes.

Cassettes were then made from this trilayer film using a production former. Since the former is 10⅞" (27.6 cm) wide, two of the 8" (20.3 cm) films were spliced together using a thermally stable polyester splicing tape. The cassettes were prepared as configured in FIGS. 3A and 3B, and were fabricated by blow molding between two forming plates. The forming plates of the production former were two aluminum mold halves which were provided with a 2 by 5 array of cavities each appropriate to the shape of the final desired shape of the top and bottom halves of the cassette respectively.

These plates were mounted in a hydraulic press, and provision made to heat the plates by cartridge heaters within the respective platens supporting the plates. At the completion of the heating phase, cooling water was circulated through the backing of the plates to quench the thermoformed construction rapidly. The two films were placed over the bottom mold half with their Surlyn™ surfaces in contact with each other, and their Attane surfaces facing the mold plates, which were initially at room temperature. Two small (1/16" dia) (1.6 mm) air tubes were inserted between the edges of the film in a slot cut into the mold, so as to inject air along a pair of air delivery runners cut into the mold halves. The top half of the mold was brought down on the film pair and hydraulic pressure of 6 tons (5500 kg) applied. Air pressure between the films was maintained at a pressure above about 0.42 kg/cm$^2$ (6 psi) to force the films into the mold cavities as the temperature of the plates was ramped up. The temperatures of the top and bottom mold halves were ramped up together. When the pre-set final temperature (or "formation" temperature) was reached, the cartridge heaters were turned off, and cooling water was flushed through the plates to bring them back to a lower temperature, while still maintaining hydraulic ram pressure and internal air pressure. Once a temperature was reached at which the construction was dimensionally stable, the molds were separated and the cassettes were removed.

Two pairs of these films were run on this former. On the first pair, the final plate temperatures were: 120.5° C. top plate/120° C. bottom plate; the plates were cooled to 57° C. before removing. With the second pair, the plates were heated to 107° C. top plate/108° C. bottom plate, and removed at 57° C. In both cases, an air pressure of 6 psi and a hydraulic ram pressure of 6 tons was used, with an overall cycle time of 5 minutes. Flexible cassettes, with well formed, flexible chambers, open fluid paths and strong heat seals were formed from both experiments.

EXAMPLE 2

An EO Outside Surface Layer Trilayer Film

A 375μ trilayer film consisting of a 50μ top layer of Attane™ 4602, a 275μ core layer of EVA(28% VA), and a 50 μ layer of a lower modulus ionomer (Dupont Surlyn™ AD-8255) was co-extruded using the equipment described in Example 1. The extruder conditions which prevailed are noted in Table 1.

Experiments using the laboratory-scale forming device were performed which paralleled those discussed in Example 1. The results are summarized in Table 3.

Chambers formed were complete, and were more flexible than those from the construction of Example 1. Heat seals were strong: seals did not separate, even after they were pulled to the point that the films tore.

Cassettes were then made from these films, using the production former described in Example 1. Formation temperatures were: 115.5° C. top plate/116.5° C. bottom plate;. an internal air pressure of 0.42 kg/cm$^2$ (6 psi), and a ram pressure of 6 tons (5500 kg) was used; cycle time was 5 minutes. Cassettes with well formed chambers, open fluid paths and strong heat seals were formed. The chambers of these cassettes were somewhat more flexible than those of Example 1.

EXAMPLE 3

Third Trilayer Film

A 375μ trilayer film consisting of a 50μ layer of Attane 4602, a 275μ layer of EVA (28% VA) and a 50 μ layer of Surlyn AD-8255 was co-extruded, using a 30 cm wide die. The center EVA layer was supplied to a Cloeren feed block from a 3.2 cm Brabender Extruder (C.W. Brabender Instruments, South Hackensack, N.J.) with a positive displacement pump. The Surlyn and Attane were supplied from 2.5 cm Wayne extruders (Wayne Machine and Die Co. of Totoya, N.J.) with 1.168 cc Zenith PEP pumps. The layered feed was then fed through a 30 cm single manifold extrusion die (Extrusion Dies, Inc. of Chippewa Falls, Wis.) The co-extruded melt was cast onto a 10 cm diameter chrome roll kept at room temperature, and then run through a nip between a rubber roll and the chrome roll. The run speed was 2 meters/min. Extruder conditions are shown on Table 1.

Cassettes were prepared on the production former, as described in Example 1, except that final formation temperatures on the plates were 99° C. on the top plate and the bottom plate. An array of flexible, apparently well formed cassettes was obtained, that appeared to have good fluid seals and channels between chambers.

Samples of these cassettes were connected with IV tubing, and then tested for performance in a 3M AVI 200A IV Infusion Pump. The tubing connected to the inlet of the cassette was connected through a syringe/luer lock to an IV solution bag, placed 46 cm above the pump. The exit tube from the cassette was run to the top of a 50 ml burette, with the top of the burette level with the bottom of the pump. The cassette was primed by first sealing the exit tube with a clamp and then squeezing the air out of the cassette and filling with fluid from the bag. The cassette was inserted in the infusion pump and the door was closed. The pump was set to a volume limit of 49 ml and a pumping rate of 500 ml/hour, and then activated. The water delivered by the pump and cassette combination was collected in the burette and measured. The pump/cassette combination delivered 49 ml and then stopped.

The same cassette was then endurance tested. A closed loop was made by connecting both ends of the tubing to an IV bag. The pump was set to pump at the maximum rate (999 ml/hr) and maximum pressure and pumped continuously for 72 hours. During that period, the cassette appeared to be functioning perfectly and showed no sign of fluid leakage or internal rupture of seals.

EXAMPLE 4

Low Modulus EMAZ Trilayer Film

A 375μ trilayer film consisting of a 50μ layer of Attane 4602, a 275μ layer of EVA (28% VA) and a 50μ layer of a very low modulus ionomer, Dupont Surlyn 8320 was co-extruded, using the 30 cm extruder/die described in Example 3. Extruder conditions are given in Table 1.

Cassettes were made from these films on the production former, varying the formation conditions to begin seeking an optimum set of conditions. Formation temperatures of 104° C.±6° C. were tried; it was found to be advantageous to remove the samples from the press at temperatures as close to room temperature as possible, to minimize distortion of the chambers; in all cases, the plates were chilled immediately after reaching the final (formation temperature). Samples were produced that appeared to be well formed and sealed, and had a flexibility approaching that of cassettes made with the plasticized PVC film.

Samples of these cassettes were connected with IV tubing, and then tested for performance in a 3M AVI 200A IV Infusion Pump in the manner described in Example 3. Some of the samples appeared to pump adequately, but continued to drip after the pump was shut off. These samples were cross-sectioned in the fluid paths between the chambers, and examined under an optical comparator (Nikon Profile Projector Model V-12, with a Nikon SC-102 digital readout scanner). It was found that there was a slight distortion of the films in the corner of the fluid path (FIG. 3a, reference numeral 33) in those cassettes which had not shut off completely. Mechanical valves close on these fluid paths and are supposed to press the two films completely together. However, this slight distortion around the heat seals is enough to prevent the fluid path from being completely closed off with the closing force of the current pump. This defect occurred in some but not all of the cassettes within a molding array, and is correctable by tuning the forming process, i.e., by making adjustments to get uniform sealing temperatures, seal force, and proper heating rate, and the like.

EXAMPLE 5

A Five Layer Film and Cassette

In an endeavor to structurally account for the slight internal distortion of the films during the forming process, a five-layer modification of Example 4 was made. It is believed that at least some of the distortion described in Example 4 is a result of distortion, or possibly flow-out of the soft EVA in areas adjacent to the heat seals. To try to reduce this, a single 25μ layer of the higher softening temperature Attane 4602 copolymer was added to the center of the EVA core. Thus a construction of: 50μ Attane 4602/ 100μ EVA(28% VA) 25μ Attane 4602/125μ EVA(28% VA)/ 75μ Surlyn 8320 was made. First a trilayer of 50μ Attane/ 100μ EVA/25μ Attane was co-extruded on a 91 cm extruder. A two manifold die was modified to accomplish this. Attane was delivered to the top manifold of the die directly from a 3.2 cm extruder (Killion KLV-125 L/D 30:1, from Killion, Inc. of Verona, N.J.) using a conventional screw. The EVA was extruded from a 6.4 cm extruder (L/D 30:1 from HPM Corporation of Mt. Gilead, Ohio) through a feed tube and feed block to the lower manifold of the two chamber co-extrusion die. The lower (25μ) Attane layer was added by feeding from a 2.5 cm extruder through a 1.25 cm tap in the bottom of the feed tube to the lower manifold. A pigment was added to the lower Attane layer to help determine distribution of the layer, and to distinguish it from the other layers in a microscopic examination of the film crosssection. The lower two-component melt then was Joined with the upper Attane layer at the exit to the die. The melt was cast onto a 40 cm chrome roll maintained at room temperature and then passed through a nip between a teflon roll and the chrome roll. Run speed was 2 m/minute. The five layer construction was then completed by co-extruding a 125μ EVA/75μ Surlyn layer onto the first trip film, with the Surlyn being supplied from the 3.2 cm extruder and the EVA from the 6.4 cm extruder. Various casting roll temperatures were tried, but it was found that room temperature on the roll produced an excellent film. Second trip run speed was also 2 m/minute. Extruder conditions are given in Table 1. This film was slit to 27.6 cm.

Cassettes were made from this film, using the production former. Two sets of cycle conditions were used, which conditions are summarized in Table 4.

Sample cassettes were taken from various plate locations within each impression, and from the same location in several impressions. These were connected into a complete IV set and volumetrically tested. A modification of the volumetric test of Example 3 was used. As in Example 3, the IV bag was 46 cm above the top of the pump; the water was pumped into the top of a 50 ml burette; the top of the burette was 76 cm"below the IV bag. The pump was set to deliver 40 ml and fluid was pumped at a rate of 500 ml/hour. The fluid delivered was then measured in the burette. Following this delivery, the pump automatically goes into a very low rate pumping cycle of 1.0 ml/hour, which is called "keep the vein open (KVO)". Its purpose is to continue delivering a small volume of fluid to the vein to prevent occlusion within the needle. The additional fluid delivered during 20 minutes of this cycle was then collected and recorded, and from this, a KVO delivery rate was calculated. Table 5 is a summary of the volumetric accuracy of these randomly selected samples. The first column lists the actual volumes delivered, when the pump had been set to deliver 40 ml. The second column lists the measured rate of delivery during the KVO cycle. (The desired KVO rate is 1.0 ml/hour.)

EXAMPLE 6

A Five-Layer Low Melt Film and Cassette

A five-layer film sample was made in which a different ethylene/octane copolymer, the lower melt index Dow Attane 4601, was substituted for the Attane 4602 of Example 5. The purpose of this substitution was to minimize the tendency of the film to fill tiny vent holes in the forming plate, that occurs after repeated forming with film having a 4602 release layer. This film was extruded on the 20 cm extruder of Example 1, using a two trip process similar to that of Example 5.

Extruder conditions are listed in Table 1. This film was tested on the laboratory former, described in Example 1. 0.42 kg/cm² (6 psi) internal pressure was used. When the sample was heated to a final temperature of 97° C., there was nearly complete chamber formation, and a strong heat seal was formed. There was complete chamber formation at 102° C. The film released easily from the aluminum forming plate.

EXAMPLE 7

A Five-Layer EB Film and Cassette

A five-layer film sample was made in which an ethylene-butane copolymer (Exxon Exact 4028) was substituted for the EVA of Example 5. This film was extruded in the manner of Example 6 (Extruder conditions listed in Table 1), and tested on the laboratory former described in Example 1. Internal pressure of 0.42 kg/cm² (6 psi) was used. At a formation temperature of 94° C., there was nearly complete formation, with good heat seals. At a formation temperature of 102° C., there was complete formation with good heat seals.

EXAMPLE 8

Comparative Single Layer Film

A 375μ film of pure EVA (28% VA) (Quantum UE-645-04) was extruded from the 30 cm extruder setup of Example 3 (using only the Brabender Extruder). Cassettes were made on the production former, using formation temperatures ranging from 64°-70° C., and a total cycle time of 2.5 to 3.5 minutes (Table 1). Cassettes were formed that exhibited medium to low seal strength (1.8 kg tensile at 70° C. forming temperature; 0.70 kg tensile at 64° C. forming temperature). They had a high adhesion to the mold, and had a somewhat tacky surface feel.

EXAMPLE 9

Comparative Single Layer Film

A 375μ film was made of an ethylene/butene copolymer (Exxon Exact 4024) from a single chamber of the 8" extruder of Example 1. (Conditions: Table 1.) These films were tested on the laboratory former to determine the best formation temperature. Results of these tests are summarized in Table 6.

Films were spliced together in the manner of Example 1 and an attempt was made to form cassettes on the production former, with three different formation temperatures. The results are summarized in Table 7. Under these conditions, chamber formation varied across a single plate from partial formation (dome) to complete formation with bases broken off adjacent to the heat seals. Heat seals between the films were very strong at the highest formation temperatures; the films showed moderate adhesion to the forming plate.

EXAMPLE 10

Comparative Single Layer Film

A 375μ film was made of an ethylene-methyl acrylate copolymer (EMAC 2205, commercially available from Chevron Chemical Co. of Houston, Tex.), using the center manifold of the 20 cm extruder of Example 1. Extruder conditions are listed in Table 1. Laboratory tests were run on this film, using the methods described in Example 1. In all tests, 0.42 kg/cm² (6 psi) internal pressure was used. Complete formation occurred at 77° C., with a thin but intact chamber formed. However, there was considerable flow out in the area under the o-ring (the "heat seal area"). In this area, only a thin film was left. At 85° C. a similar formation occurred, with a very thin layer left in the heat seal area, and a slightly thinner bottom on the chamber. At 96° C., the heat seal area had broken through entirely, and the chamber separated completely from the rest of the film. Adhesion to the mold was low in all three cases. Two of these films were spliced together as described previously, and tested on the production former. With final formation temperatures of: bottom plate: 86° C., top plate: 90° C., partial formation occurred. There was separation of the "chambers" (actually domes) at their bases on some of the impressions. There appeared to be strong heat sealing of the two films in all areas of the plate. The samples came out of the mold with low adhesion.

EXAMPLE 11

Comparative Single Layer Film

A 375μ film was made of another ethylene-methyl acrylate copolymer (EMAC 2260, commercially available from Chevron Chemical Co. of Houston, Tex.) using the center manifold of the 20 cm extruder of Example 1. Extruder conditions are listed in Table 1. Laboratory tests showed that there was partial formation at 88° C. and 0.42 kg/cm² (6 lbs) pressure with a good heat seal. The dome that formed was stiff, compared to the EMAC 2205. Adhesion to the mold was low.

EXAMPLE 12

A Tri-Layer Film

A tri-layer film was formed under circumstances wherein the core layer also acted as an inside surface layer. In this case, the first thermoplastic polymer used also had appropriate self-bonding and tensile strength characteristics. The film included a 50μ layer of Attane 4602 and an 275μ layer of an ethylene-butene Copolymer (and EB copolymer of the tradenee Exact 4024). The film was made on the 30 cm extruder by the process described in Example 3, with the third extruder that supplied the Surlyn turned off. The film was soft and flexible, and formed cassettes using a formation temperature of 102° C. Unlike the single layer Exact 4024 film of Example 9, this tri/bi-layer film did not adhere to the aluminum mold. The Attane 4602 at these formation temperatures, acted as a "mold-release", and did not appear to adversely affect the ability of the softer and tackier EB to take the shape of the mold. Extruder conditions are listed in Table 1. Samples of this film were tested on the laboratory former. A formation temperature of 102° C. was used with 0.42 kg/cm² (6 psi) of internal pressure. Complete formation occurred, with strong heat seals, not only under the o-ring, where pressure was applied, but wherever the films came in contact. The chamber formed looked quite uniform, and was quite optically clear.

EXAMPLE 13

An EMAC Tri/Bi-Layer Film and Cassette

A trilayer film was formed under circumstances where the core layer also acted as an outside surface layer. In this case, the first thermoplastic polymer used also had appropriate mold release and abrasion resistance characteristics. The film included 275μ of ethylene-methyl acrylate copolymer (EMAC 2205) and 100μ Surlyn (EMAZ 8320). The film was made on the 30 cm extruder of Example 3. Extruder conditions are listed in Table 1. Samples of this film were tested on the laboratory former. Samples were formed at 77° C. and 0.42 kg/cm² (6 psi) of internal pressure. Chamber and seal formation were complete. The addition of Surlyn 8320 appears to have strengthened the film in both the chamber and heat seal areas, compared to cassettes made from EMAC alone, see Example 10.

The Surlyn adds both a degree of toughness and dimensional stability to the film without greatly increasing its stiffness. The EMAC 2205 softens at 58° C. and melts at 83° C. The Surlyn 8320 seals at 72° C. Thus this combination makes it possible to use a lower formation temperature (77° C.) than in the previous Examples (92° C.). Further, in this Example, the overall film softening and sealing temperatures are closer together than in the previous Examples. Note that the EMAC in this material is acting as both core and outer surface/release layer.

EXAMPLE 14

An EMAC/Blended EVA Trilayer Film

A trilayer film of 50μ EMAC 2205, 225μ of a blend of 75% EVA (28% VA)/25% EVA (19% VA), and 100μ of Surlyn 8320 was made on the 30 cm extruder of Example 3. The two EVA resins were blended by hand, and then added to the hopper of the center layer Brabender extruder. The extruder conditions are listed in Table 1. Samples of this film were tested on the laboratory-scale former with a temperature of 74° C. and a pressure of 0.42 kg/cm$^2$ (6 psi). Complete formation occurred, with strong heat seals. The film assembly released readily from the aluminum plates.

EXAMPLE 15

An EO Trilayer Film

An ABC trilayer film was made from Attane 4602 (A) (50μ), ethylene-methyl acrylate copolymer (EMAC 2205) (B) (225μ), and Surlyn AD-8255 (C) (50μ), using the 20 cm extruder described in Example 1. Extruder conditions are listed in Table 1. Laboratory-scale tests were run on this film, using the methods of Example 1. At a formation temperature of 96° C., there was nearly complete formation with excellent heat seals. At 102° C., there was complete formation with excellent heat seals. Two of these films were spliced together as described previously, and tested on the production former. 0.42 kg/cm$^2$ (6 psi) of internal pressure was used. Formation temperatures were: bottom plate 113° C. top plate 108° C. Partial formation occurred, but there was no sign of the weakened chamber bases found in Example 10 with the EMAC alone. Strong heat sealing occurred only in the areas where heat sealing is expected, i.e., the fluid seals on the perimeter of the chambers and connecting fluid paths.

EXAMPLE 16

Adhesive Bonding of Tubing and Cassette

Tubing made according to Example 8 of U.S. patent application Ser. No. 08/103,328, U.S. Pat. No. 5,562,127 cited above, was bonded to a cassette prepared according to Example 5 above. The two components of a two-part epoxy adhesive commercially available as TRA-BOND FDA-2 from Tra-Con, Inc. of Medford, Mass., were mixed and a small amount was applied to one end of the tube. This treated end was inserted into one of the molded tubes in the cassette, and the assembly allowed to cure for 15 minutes at 65° C., and then for 12 hours at 25° C.

EXAMPLE 17

Testing of Assembly

The assembly of Example 16 was tested for bond strength and integrity by filling the lumen of the tube and the cassette with air, and subjecting the air to a pressure of 10 psi (0.70 kg/cm$^2$). The bond was submerged in water and examined visually for leaks revealed by emitted bubbles. After the visual inspection, the pressure was released, and an 8 pound (3.6 kg) weight was hung from the assembly so as to stress the bond. The assembly was visually inspected for signs of bond separation. Then the lumen of the tube and the cassette was repressurized with air to a pressure of 10 psi. Again, the bond was submerged and examined visually for leaks. Bonded constructions according to Example 16 were able to successfully pass the three aspects of this test, and were thus deemed to be suitable for use in medical tubing assemblies.

EXAMPLE 18

TriLayer EMAC/SURLYN Blend Film and Cassette

A tri-layer film sample of 50μ of EMAC 2205, 225μ of a blend of 70% EMAC 2205/30% Surlyn 8320, and 100μ of Surlyn 8320 was made on the 30 cm extruder setup according to Example 3. The EMAC and Surlyn resins were blended by hand and then added to the hopper of the center layer Brabender Extruder. Extrusion conditions are described in Table 1. The film was tested on the laboratory-scale former according to Example 1, with an internal pressure of 0.42 kg/cm$^2$ (6 psi) and a temperature of 77° C. being used. Complete formation occurred with strong heat seals, and a ready release from the plate.

EXAMPLE 19

Tri/Bilayer Film and Cassette

A tri/bilayer film sample of 50μ of EMAC 2205 and 325μ of Surlyn 8320 was made on the 30 cm extruder setup according to Example 3. Extrusion conditions are described in Table 1. The film was tested on the laboratory-scale former according to Example 1, with an internal pressure of 0.42 kg/cm$^2$ (6 psi) and a temperature of 79° C. being used. Complete formation occurred with strong heat seals. The cassette was quite flexible, and appeared to spring back readily after being compressed by hand.

EXAMPLE 20

TriLayer EVA Film and Cassette

A trilayer film sample of 50μ of EMAC 2205, 225μ of EVA (28% VA), and 100μ of Surlyn 8320 was made on the 30 cm extruder setup according to Example 3. Extrusion conditions are described in Table 1. The film was tested on the laboratory-scale former according to Example 1, with an internal pressure of 0.42 kg/cm$^2$ (6 psi) and a temperature of 77° C. being used. Complete formation occurred with strong heat seals, and the films released readily from the plate.

EXAMPLE 21

Adhesive Bonding of Tubing and Cassette

Tubing and a cassette according to Example 16 above were bonded to each other, but this time with a cyanoacrylate adhesive commercially available as Permabond from National starch and Chemical Corporation of Englewood, N.J. A small amount of the adhesive was applied to one end of the tube, and the treated end was inserted into one of the molded tubes in the cassette. The construction was then allowed to complete the cure for 12 hours at 25° C. The bond was then tested in the fashion described in Example 17, and found to have bond strength and integrity and adequate for its purpose in medical tubing assemblies.

EXAMPLE 22

Epoxy Bonding of Tubing and Cassette

Tubing and a cassette according to Example 16 above were bonded to each other, but this time with a UV curing epoxy adhesive commercially available as UV6010 from Polychem Corp. of Cranston, R.I. A small amount of the adhesive was applied to one end of the tube, and the treated end was inserted into one of the molded tubes in the cassette. The treated area was then subjected to high intensity UV light shown through the wall of the cassette for one second. The assembly was then allowed to complete the cure for 12 hours at 25° C. The bond was then tested in the fashion described in Example 17, and found to have bond strength and integrity and adequate for its purpose in medical tubing assemblies.

EXAMPLE 23

Second Epoxy Bonding

Tubing and a cassette were bonded according to Example 19, with the exception that the UV curing epoxy adhesive was instead one commercially available as L-4240 from ICI of Wilmington, Del. Adequate bond strength and integrity was achieved.

EXAMPLE 24

Susceptor Particle Bonding of Tubing and Drip Chamber

One sixteenth inch (1.6 mm) glass fibers commercially available as 739 DD from Corning Co. of Corning, N.Y. were coated with a thin layer of stainless steel as described in U.S. patent application Ser. No. 07/668,974 U.S. Pat. No. 5,529,708 to form susceptor particles. These fibers were mixed into an ionomer commercially available as Surlyn AD 8255 from E. I. Dupont and Nemours of Wilmington, Del. at a volume loading of 20%. A Haake Rheocord System Model 600, commercially available from Haake of Saddlebrook, N.J., was used to make this composite. A small amount of blue pigment concentrate in low density polyethylene was also used to give the composite a blue color. This composite is the susceptor particle filled bonding material.

A strip of this susceptor particle filled bonding material which was about 0.010" (0.25 mm) thick and 3 millimeters wide was placed around the tip of a polypropylene drip chamber commercially available from Medlon of Burbank, Calif. Tubing made according to Example 46 of U.S. patent application Ser. No. 08/103,328, U.S. Pat. No. 5,562,127 cited above, e.g., a three layer tubing with Surlyn AD 8255 on the inside and outside surfaces and Quantum UE645 EVA in the core, was slipped over this.

This assembly was placed in a small coil of a Lepel T-2.5-1-MC-B3W(T) induction heater, commercially available from Lepel, of Edgewood, N.Y., set to the 5 to 8 MHz frequency range. The induction heater had a grid control setting of 66, plate current of 0.50 amps, and grid current of 142 milliamps. The coil was oval, in shape with 4 turns of ⅛ inch (3.2 mm) outside diameter tubing with inside opening of 1½" (3.8 cm) wide by ⅞" (2.2 cm) high by ⅝" (1.6 cm) deep. Power to the induction heater coil was turned on for 2.25 seconds. This melted the susceptor particle filled bonding material and the surfaces of the tubing and drip chamber, forming a good bond. This bond then passed subsequent testing as described in Example 17 for bond strength and leak integrity.

EXAMPLE 25

Susceptor Particle Bonding of Tubing and Luer Lock

Glass fibers coated with a thin layer of stainless steel as described in Example 24 were incorporated into a hot melt adhesive commercially available as Euremelt 2140 from Schering-Berlin of Lakeland, Fla., at a volume loading of 20%. A strip of this susceptor particle filled bonding material which was about 0.010" (0.25 mm) thick and 3 millimeters wide was placed around the end of a piece of the trilayer tubing described in Example 24. This tubing with bonding material was slipped into a luer lock made of ABS. This was placed in the induction heater coil described above and power was applied to the coil for 2.5 seconds. This heated the susceptor particle filled bonding material and bonded the tubing to the luer lock. This bond then passed subsequent testing according to Example 17 for bond strength and leak integrity.

EXAMPLE 26

Susceptor Particle Bonding of Tubing and Drip Chamber

Glass fibers coated with a thin layer of stainless steel as described in Example 24 were incorporated into a hot melt adhesive commercially available as JetMelt 3748 from the 3M Company of St. Paul, Minn., at a volume loading of 20%.

A strip of this susceptor particle filled bonding material which was about 0.010" (0.25 mm) thick and 3 millimeters wide was placed around the tip of a polypropylene drip cheer commercially available from Medlon of Burbank, Calif. Tubing made according to Example 8 of U.S. patent application Ser. No. 08/103,328, U.S. Pat. No. 5,562,127 cited above, e.g., a trilayer tubing with Surlyn 8320 on the inside and outside surfaces and Exact 4028 EB in the core, was slipped over this.

A model 2274A microwave generator commercially available from Litton of Memphis, Tenn. was set to deliver 700 watts at a frequency of 2.45 gigahertz for 60 seconds. The bond thus created then passed subsequent testing according to Example 17 for bond strength and leak integrity.

EXAMPLE 27

Susceptor Particle Bonding of Tubing and Cassette

A susceptor particle bonded assembly was prepared as in Example 24, except that the tubing was bonded to a cassette made according to Example 16. This bond then passed subsequent testing according to Example 17 for bond strength and leak integrity.

EXAMPLE 28

Susceptor Particle Bonding of Tubing and Chamber

Ferromagnetic amorphous powders were been produced as described in U.S. patent application Ser. No. 07/800,632 U.S. Pat. No. 5,278,377 to form susceptor particles. The susceptor particles had an alloy composition of $Fe_{68.5}Cr_{8.5}P_{15}C_5B_3$ (in atomic percentage). These powders have a Curie temperature of ≠130° C. and particle sizes below 44 micron (or below 325 mesh). These powders were mixed into Quantum UE645 EVA at a volume loading of 8%. A small amount of green pigment concentrate in low density polyethylene was also used to give the final composite a green color. This mixture was compounded in a two rolls rubber mill manufactured by S. Bolling, Cleveland, Ohio, and extruded into tubings having approximately a 10 mil (0.25 mm).wall thickness, and 0.150" (3.8 mm) outside diameter. These tubings become the amorphous powders filled bonding materials.

A piece of this bonding material which was about 3 millimeters long was placed into the tip of a polypropylene drip chamber as described in Example 23. Tubing made according to Example 46 of U.S. application Ser. No. 08/103,328, U.S. Pat. No. 5,562,127 cited above, e.g. a trilayer tubing with Surlyn AD 8255 on the inner and outer surfaces and Quantum UE6645 EVA in the core, was slipped over this.

A dozen samples of this assembly were placed in a rectangular coil of an Emabond P-005-09 induction heater set. This Emabond system has a five kilowatt power supply in the 3 to 7 MHz frequency range. The coil is rectangular shape with 3 turns of 6"×2". Power to the induction heater coil was energized for about 30 seconds. This melted the bonding materials and the surfaces to the tubing and drip chamber, forming a good bonding. This bond passed subsequent testing as described in Example 17 for bond strength and leak integrity.

EXAMPLE 29

Susceptor Particle Bonding of Tubing and Cassette

Ferromagnetic powders as described in Example 28 were mixed into an ionomar commercially available as Surlyn 1702 from E. I. Dupont and Nemours of Wilmington, Del. at a volume loading of 8%. A C. W. Brabender model 5000 mixer was used to make this composite. Portion of this composite was then hot pressed by using a Carver Laboratory Press model 2699 commercially available from F. S. Carver of Wabash, Ind. into a thin sheet of about 0.010" (0.25 mm) thickness. This sheet of composite is the susceptor powder filled bonding materials.

A strip of this ferromagnetic amorphous powder filled bonding material which was about 0.010" (0.25 mm) thick and 3 millimeter wide was placed around the tubing which was made according to Example 10 of US application Ser. No. 08/103,328, U.S. Pat. No. 5,562,127 cited above, e.g. a three layer tubing with Surlyn 9320 on the inner and outer surfaces and Exact 4028 the core. This tubing with the bonding material was slipped into an cassette which was made according to Example 5 above. Several of these assemblies were placed in the induction heater as described in Example 28 for 30 seconds. This melted the bonding materials and the surfaces to the tubing and cassette, forming a good bonding. This bond passed subsequent testing as described in Example 17 for bond strength and leak integrity.

EXAMPLE 30

Susceptor Particle Bonding Tubing and Cassette

A bond assembly was prepared according to the procedure of Example 28, except that the tubing was bonded to a cassette prepared according to Example 5 above. This bond passed subsequent testing as described in Example 17 for bond strength and leak integrity.

EXAMPLE 31

Susceptor Particle Bonding of Tubing and Chamber

A bonded assembly was prepared a Example 29, except that the tubing was bonded to a drip chamber as described in Example 28. This bond passed subsequent testing as described in Example 17 for bond strength and leak integrity.

EXAMPLE 32

Susceptor Particle BondinG of Tubing and Luer Lock

A bonded assembly was prepared according to the procedure of Example 28, except the tubing was bonded to a luer lock. This bond passed subsequent testing as described in Example 17 for bond strength and leak integrity.

EXAMPLE 33

Susceptor Particle Bonding of Tubing and Luer Lock

A bond assembly was prepared as in Example 29, except that the tubing was bonded to a luer lock fabricated from ABS polymer. This bond passed subsequent testing as described in Example 17 for bond strength and leak integrity.

EXAMPLE 34

Particle Bonding of Single Layer Tubing to Drip Chamber

Suzorite mica flakes, from Suzorite Mica Products, Inc. in Hunt Valley, Md., were coated with a thin layer of stainless steel as described in U.S. patent application Ser. No. 07/668, 974 U.S. Pat. No. 5,529,708 cited above. These coated mica flakes were then mixed into Quantum UE645 EVA (28% vinyl acetate) at a volume loading of 10%. Red pigment and titanium dioxide were added to the composite to impart a red color. A thin layer of this coated particle susceptor bonding material was placed in the bond area of a drip chamber made from Rexerie 1903 EVA (9% vinyl acetate). Tubing made from Quantum UE645 EVA was placed over this. This assembled component was placed in the coil of the LEPEL induction heater for 2.25 seconds. The coil was made with $\frac{1}{8}$" (3 mm) OD copper tubing. It had 5 turns, the inner diameter of the coil was 0.5" (13 mm), the length of the coil was $\frac{7}{8}$" (22 mm). The settings on the LEPEL were Grid Control 76, plate current 0.48 amps, grid current 120 milliamps. The susceptor filled bonding material heated and bonded the two components together, so that it passed the test described in Example 17.

EXAMPLE 35

Five-Layer Film and Cassette

A five-layer film sample was made according to Example 5, except that zinc-doped, low modulus Surlyn 9320 was substituted for the Surlyn 8320. Extrusion conditions are described in Table 1. The film was tested on the laboratory-scale former according to Example 1, with an internal pressure of 0.42 kg/cm$^2$ (6 psi) being used. At a formation temperature of 94° C., there was partial formation; at a formation temperature of 101° C., there was complete formation with good heat seals.

EXAMPLE 36

EMAC TriLayer Film and Cassette

A trilayer film sample of 50µ of Attane 4601, 275 µ of EMAC 2260 and 50µ of Surlyn AD 8255 was made on the 30 cm extruder setup according to Example 3. Extrusion conditions are described in Table 1. The film was tested on the laboratory-scale former according to Example 1, with an internal pressure of 0.42 kg/cm$^2$ (6 psi) and a temperature of 99° C. being used. Complete formation occurred with strong heat seals, excellent release from the plate, and excellent clarity.

EXAMPLE 37

Susceptor Particle Enhanced Curing of Epoxy

Glass fibers coated with a thin layer of stainless steel were made according to Example 21 above forming susceptor particles which were mixed into TRA-BOND FDA-2 epoxy, discussed in Example 16 above, at a loading of 20%. This loaded epoxy was applied to the ends of tubing made according to Example 8 of U.S. patent application Ser. No. 08/103,328 U.S. Pat. No. 5,562,127 cited above, and these ends were inserted into a Y-sites fabricated from ABS polymer. Care was taken to keep the thickness of the epoxy mixture on the tubing uniform. These constructions were placed in the coil of the LEPEL induction heater described above in Example 24, and the heater was energized for 25 seconds. This heated the epoxy/coated fiber mixture enough to cure it slightly. The green strength in these treated samples was greater than control samples made without the use of susceptor particles.

TABLE 1

| | EXAMPLE # | | | | | | | | | | | |
|---|---|---|---|---|---|---|---|---|---|---|---|---|
| | 1 | | | 2 | | | 3 | | | 4 | | |
| | LAYER | | | | | | | | | | | |
| | OUTER | CORE | INNER | OUTER | CORE | INNER | OUTER | CORE | INNER | OUTER | CORE | INNER |
| | MATERIAL | | | | | | | | | | | |
| | E.O. (ATTANE 4602) | EVA (28% VA) | SUR-LYN 1702 | E.O. (ATTANE 4602) | EVA (28% VA) | SUR-LYN AD-8255 | E.O. (ATTANE 4602) | EVA (28% VA) | SUR-LYN AD-8255 | E.O. (ATTANE 4602) | EVA (28% VA) | SUR-LYN 8320 |
| | EXTRUDER BARREL | | | | | | | | | | | |
| ZONE 1 TEMP °C. | 121 | 121 | 135 | 121 | 121 | 135 | 121 | 121 | 121 | 121 | 121 | 121 |
| ZONE 2 TEMP | 149 | 157 | 163 | 149 | 157 | 163 | 149 | 157 | 149 | 157 | 157 | 157 |
| ZONE 3 TEMP | 176.5 | 176.5 | 176.5 | 176.5 | 176.5 | 176.5 | 176.5 | 176.5 | 176.5 | 176.5 | 176.5 | 176.5 |
| ZONE 4 TEMP | 176.5 | 179.5 | 176.5 | 176.5 | 179.5 | 176.5 | 176.5 | 179.5 | 176.5 | 196 | 196 | 196 |
| ZONE 5 TEMP | | 182 | | | 182 | | 176.5 (gate) | 182 (gate) | 176.5 (gate) | 196 (gate) | 196 (gate) | 196 (gate) |
| CAST ROLL TEMP | | 12° | | | 12° | | | | | | | |
| SCREW RPM | 3.2 | | 3.7 | 3.2 | | 3.6 | | | | | | |
| LINE SPEED | | 0.85 M/MIN | | | 0.85 M/MIN | | | | | | | |
| MODULUS (LAYER) (MPa) | 26.9 | | 117.0 | 26.9 | | 71.0 | 26.9 | | 71.0 | 26.9 | | |
| STRESS AT 50% STRAIN (LAYER) (MPa) | 3.5 | | 7.0 | 3.5 | | 6.1 | 3.5 | | 6.1 | 3.5 | | |
| MODULUS (COMPOSITE) (MPa) | | 42.7 | | | 36.0 | | | 36.0 | | | 27.0 | |
| STRESS AT 50% STRAIN (COMPOSITE) (MPa) | | 4.1 | | | 3.8 | | | 3.8 | | | 3.8 | |

| | EXAMPLE # | | | | | | | | | |
|---|---|---|---|---|---|---|---|---|---|---|
| | 5 | | | | | 6 | | | | |
| | LAYER | | | | | | | | | |
| | OUTER | CORE | CENTER | CORE | INNER | OUTER | CORE | CENTER | CORE | INNER |
| | MATERIAL | | | | | | | | | |
| | E.O (ATTANE 4602) | EVA (28% VA) | E.O (ATTANE 4602) | EVA (28% VA) | SURLYN 8320 | E.O (ATTANE 4601) | EVA (28% VA) | E.O (ATTANE 4601) | EVA (28% VA) | SURLYN 8320 |
| | EXTRUDER BARREL | | | | | | | | | |
| ZONE 1 TEMP °C. | 121 | 121 | 121 | 121 | 121 | 121 | 121 | 121 | 121 | 121 |
| ZONE 2 TEMP | 157 | 157 | 157 | 157 | 157 | 157 | 157 | 157 | 157 | 157 |
| ZONE 3 TEMP | 176.5 | 176.5 | 176.5 | 176.5 | 176.5 | 176.5 | 176.5 | 176.5 | 176.5 | 176.5 |
| ZONE 4 TEMP | 196 | 196 | 196 | 196 | 196 | 196 | 196 | 196 | 196 | 196 |
| ZONE 5 TEMP | 196 | 196 | 196 (gate) | 196 | 196 | 196 | 196 | 196 (gate) | 196 | 196 |
| CAST ROLL TEMP | | R.T. | | R.T. | | | R.T. | | R.T. | |
| SCREW RPM | | | | | | | | | | |
| LINE SPEED | | | 1.8 M/MIN | | | | | 0.82 M/MIN | | |
| MODULUS (LAYER) (MPa) | 26.9 | | 26.9 | | | 26.9 | | 26.9 | | |
| STRESS AT 50% STRAIN (LAYER) (MPa) | 3.5 | | 3.5 | | | 3.5 | | 3.5 | | |
| MODULUS (COMPOSITE) (MPa) | | | 37.8 | | | | | 33.1 | | |
| STRESS AT 50% STRAIN (COMPOSITE) (MPa) | | | 4.2 | | | | | 4.2 | | |

TABLE 1-continued

| | EXAMPLE # | | | | | | | | | |
|---|---|---|---|---|---|---|---|---|---|---|
| | 7 | | | | 8 | 9 | 10 | 11 | 12 | |
| | LAYER | | | | | | | | | |
| | OUTER | CORE | CENTER | CORE | INNER | | | | OUTER | CORE |
| | MATERIAL | | | | | | | | | |
| | E.O. (ATTANE 4602) | E.B. (EXACT 4028) | E.O. (ATTANE 4602) | E.B. (EXACT 4028) | SURLYN 8320 | EVA (28% VA) | E.B. (EXACT 4024) | EMAC (2205) | EMAC (2260) | E.O. (ATTANE 4602) | E.B. (EXACT 4024) |
| | EXTRUDER BARREL | | | | | | | | | |
| ZONE 1 TEMP °C. | 121 | 121 | 121 | 121 | 121 | 121 | 129 | 121 | 121.5 | 121 | 129.5 |
| ZONE 2 TEMP | 157 | 157 | 157 | 157 | 157 | 157 | 176.5 | 158.5 | 159.5 | 149 | 176.5 |
| ZONE 3 TEMP | 176.5 | 176.5 | 176.5 | 176.5 | 176.5 | 176.5 | 190.5 | 180 | 180.5 | 176.5 | 190.5 |
| ZONE 4 TEMP | 196 | 196 | 196 | 196 | 196 | 179.5 | 193 | 194 | 193 | 176.5 | 193 |
| ZONE 5 TEMP | 196 | 196 | 196 (gate) | 196 | 196 | 182 (gate) | | 193 | 193 | | |
| CAST ROLL TEMP | | R.T. | | R.T. | | 10 | | | | | |
| SCREW RPM | | | | | | | | 210 | 206 | 205 | 5.9 | 210 |
| LINE SPEED | | | 0.82 M/MIN | | | 0.76 | | 0.79 | 1.1 | | |
| MODULUS (LAYER) (MPa) | | | | | | 26.9 | 29.4 | 33.4 | 47.8 | 29.4 | |
| STRESS AT 50% STRAIN (LAYER) (MPa) | | | | | | 3.5 | 3.8 | 4.0 | 4.5 | 3.8 | |
| MODULUS (COMPOSITE) (MPa) | | | 31.5 | | | | | | | 34.0 | |
| STRESS AT 50% STRAIN (MPa) (COMPOSITE) | | | 3.7 | | | | | | | 3.9 | |

| | EXAMPLE # | | | | | | | | |
|---|---|---|---|---|---|---|---|---|---|
| | 13 | | 14 | | | 15 | | 18 | |
| | LAYER | | | | | | | | |
| | CORE | INNER | OUTER | CORE | INNER | OUTER | CORE | | |
| | MATERIAL | | | | | | | | |
| | EMAC 2205 | SURLYN 8320 | EMAC 2205 | 75% EVA (28% VA) 25% EVA (19% VA) | SURLYN 8320 | E.O. (ATTANE 4602) | EMAC 2205 | SURLYN (AD-8255) | EMAC 2205 | 70% EMAC 2205 30% SURLYN 8320 | SURLYN 8320 |
| | EXTRUDER BARREL | | | | | | | | |
| ZONE 1 TEMP | 121 | 121 | 160 | 140 | 160 | 121 | 121 | 135 | 160 | 140 | 160 |
| ZONE 2 TEMP | 157 | 157 | 185 | 175 | 185 | 149 | 157 | 163 | 185 | 175 | 185 |
| ZONE 3 TEMP | 176.5 | 176.5 | 185 | 185 | 185 | 176.5 | 176.5 | 176.5 | 185 | 185 | 185 |
| ZONE 4 TEMP | 196 | 196 | — | 185 | — | 176.5 | 179.5 | 176.5 | — | 185 | — |
| ZONE 5 TEMP | 196 | 196 | 185 | 185 (gate) | 185 | | 182 | | 185 (gate) | 185 (gate) | 185 |
| CAST ROLL TEMP | R.T. | | | R.T. | | | 12° | | | R.T. | |
| SCREW RPM | | | | | | 3.2 | | 3.7 | | | |
| LINE SPEED | 0.91 M/MIN | | 0.91 M/MIN | | | 0.85 M/MIN | | | | 0.91 M/MIN | |
| MODULUS (LAYER) (MPa) | 33.4 | | | | | 26.9 | 117.0 | | | | |
| STRESS AT 50% STRAIN (LAYER) (MPa) | 4.0 | | | | | 3.5 | 7.0 | | | | |
| MODULUS (MPa) (COMPOSITE) | | | | | | 42.7 | | | | | |
| STRESS AT 50% STRAIN (MPa) (COMPOSITE) | | | | | | 4.1 | | | | | |

TABLE 1-continued

| | EXAMPLE # | | | | | | | | | | | |
|---|---|---|---|---|---|---|---|---|---|---|---|---|
| | 19 | | 20 | | | 35 | | | | 36 | | |
| | LAYER | | | | | | | | | | | |
| | OUTER | IN-NER | OUTER | CORE | IN-NER | OUTER | CORE | CENTER | CORE | INNER | OUTER | CORE | INNER |
| | MATERIAL | | | | | | | | | | | | |
| | EMAC 2205 | SUR-LYN 8320 | EMAC 2205 | EVA (28% VA) | SUR-LYN 8320 | E.O (ATTANE 4602) | EVA (28% VA) | E.O (ATTANE 4602) | EVA (28% VA) | SUR-LYN 9320 | E.O (ATTANE 4601) | EMAC 2260 | SURLYN AD-8255 |
| | EXTRUDER BARREL | | | | | | | | | | | | |
| ZONE 1 TEMP °C. | 160 | 160 | 160 | 140 | 160 | 121 | 121 | 121 | 121 | 121 | 160 | 140 | 160 |
| ZONE 2 TEMP | 185 | 185 | 185 | 175 | 185 | 157 | 157 | 157 | 157 | 157 | 185 | 175 | 185 |
| ZONE 3 TEMP | 185 | 185 | 185 | 185 | 185 | 176.5 | 176.5 | 176.5 | 176.5 | 176.5 | 185 | 185 | 185 |
| ZONE 4 TEMP | — | — | — | 185 | — | 196 | 196 | 196 | 196 | 196 | — | 185 | — |
| ZONE 5 TEMP | 185 (gate) | 185 | 185 (gate) | 185 (gate) | 185 | 196 | 196 | 196 (gate) | 196 | 196 | 185 (gate) | 185 (gate) | 185 |
| CAST ROLL TEMP | | | | R.T. | | R.T | | | R.T | | | R.T | |
| SCREW RPM | | | | | | | | | | | | | |
| LINE SPEED | 0.91 M/MIN | | | 0.91 M/MIN | | | | 1.8 M/MIN | | | | 0.91 M/MIN | |
| MODULUS (LAYER) (MPa) | | | | | | | 26.9 | | 26.9 | | | | |
| STRESS AT 50% STRAIN (LAYER) (MPa) | | | | | | | 3.5 | | 3.5 | | | | |
| MODULUS (COMPOSITE) (MPa) | | | | | | | | | | | | | |
| STRESS AT 50% STRAIN (COMPOSITE) (MPa) | | | | | | | | | | | | | |

TABLE 2 for Example 1

| Temperature (°C.) | Time to reach temperature (min) | Pressure (kg/cm²) | Degree of chamber formation | Degree of seal formation |
|---|---|---|---|---|
| 93 | 18 | 0.21 | partial | partial |
| 96 | 25 | 0.21 | partial | partial |
| 97 | 13 | 0.21 | partial | partial |
| 106 | 16 | 0.21 to 0.27 | complete | complete |
| 106 | 16 | 0.42 | complete | complete |
| 116 | 25 | 0.21 to 0.24 | complete | chamber formed, but collapsed |

TABLE 3 for Example 2

| Temperature (°C.) | Time to reach temperature (min) | Pressure (kg/cm²) | Degree of chamber formation | Degree of seal formation |
|---|---|---|---|---|
| 93 | 18 | 0.21 | | |
| 96 | 25 | 0.21 | | |
| 97 | 13 | 0.21 | partial | partial |
| 106 | 16 | 0.21 | partial | partial |
| 106 | 25 | 0.24 | complete | complete |
| 116 | 4 | 0.21 | complete | complete |

TABLE 4 for Example 5 Cassette forming conditions

| Process Attribute | Condition set #1 | Condition set #2 |
|---|---|---|
| Starting temperature (°C.) | 38 | 49 |
| Formation (highest) temperature (°C.) | 91.7 | 91.1 |
| Low air pressure (kg/cm²) | 0.14 | 0.21 |
| Plate temperature where low air pressure was initiated (°C.) | 40.6 | 51.7 |
| High air pressure (kg/cm²) | 0.91 | 0.91 |
| Plate temperature where high air pressure was initiated (°C.) | 7300 | 57 |
| Hydraulic ram pressure (kg) | 4:56 | 4:22 |
| Cycle time (min) | >77 | >77 |
| Seal temperature range (°C.) | >88 | >88 |
| Formation Temperature Range (°C.) | >88 | >88 |
| Seat strength (kg) | 4.5 | 4.5 |

TABLE 5 for Example 5
Volumetrics test on complete cassettes

| Condition set | Volume delivered during regular pumping (40 ml expected) | Volume delivered during "KVO" pumping (in ml/hour, 1.0 ml/hr expected) |
| --- | --- | --- |
| 1 | 40.9 | 1.1 |
| 1 | 42.7 | 2.2 |
| 1 | 42.8 | 5.9 |
| 1 | 44.0 | 11.1 |
| 1 | 40.2 | 3.0 |
| 2 | 41.5 | 1.4 |
| 2 | 43.0 | 3.0 |
| 2 | 42.9 | 8.2 |
| 2 | 41.8 | 4.7 |
| 2 | 44.0 | 2.7 |
| 2 | 45.7 | 1.1 |
| 2 | 42.9 | 1.8 |
| 2 | 39.8 | not done |

TABLE 6 for Example 9

| Formation Temperature (°C.) | Pressure (kg/cm²) | Degree of Chamber formation |
| --- | --- | --- |
| 74 | 0.42 | Partial (Dome) |
| 80.5 | 0.42 | Complete (thin walls) |
| 88 | 0.42 | Chamber collapsed |

TABLE 7 for Example 9

| Temperature of top plate (°C.) | Temperature of bottom plate (°C.) | Degree of Chamber formation |
| --- | --- | --- |
| 75 | 75 | Partial |
| 79.5 | 83 | |
| 80.5 | 84 | Complete, but with thin walls in some chambers |

While a description of the preferred weight fractions, processing conditions, and product usages have been provided by the examples, the scope of the invention is not to be limited thereto or thereby. Various modifications and alterations of the present invention will be apparent to those skilled in the art without departing from the scope and spirit of the present invention. The examples described in this application are illustrative of the possibilities of varying the amounts and types of polymeric materials in the multilayered tubings and films to achieve characteristics for specific purposes.

Consequently, for an understanding of the scope of the present invention, reference is made to the following claims.

We claim:

1. A film based assembly comprising:
  a molded structure having two sides, each side being comprised of a film having outside and inside surfaces comprising:
  a) a core layer of at least one chlorine-free first thermoplastic polymer having a flexibility, measured by its Young's modulus, less than about 60 megaPascals;
  b) an outside surface layer of at least one chlorine-free second thermoplastic polymer having a Young's modulus up to about ten times the Young's modulus of the core layer thermoplastic polymer and being capable of non-stick release from a heated surface; and
  c) an inside surface layer of at least one chlorine-free third thermoplastic polymer having a Young's modulus up to about ten times the Young's modulus of the core layer thermoplastic polymer and being capable of heat self-sealing before the core and outside surface layers become substantially deformed under heat;
  wherein the film is capable of being expanded at least in part under heat and pressure without failure of film integrity, flexibility and resilience wherein at least one of the sides being at least in part expanded; and wherein the molded structure is a cassette having molded-in fluid channels and pumping bubbles therein.

2. A film based assembly according to claim 1 wherein the molded structure is an intravenous fluid bag.

3. A method of forming a film based structure comprising:
  placing two sheets of a film having outside and inside surfaces comprising: a core layer of at least one chlorine-free first thermoplastic polymer having a flexibility, measured by its Young's modulus, less than about 60 megaPascals; an outside surface layer of at least one chlorine-free second thermoplastic polymer having a Young's modulus up to about ten times the Young's modulus of the core layer thermoplastic polymer and being capable of non-stick release from a heated surface; and an inside surface layer of at least one chlorine-free third thermoplastic polymer having a Young's modulus up to about ten times the Young's modulus of the core layer thermoplastic polymer and being capable of heat self-sealing before the core and outside surface layers become substantially deformed under heat; wherein, the film is capable of being expanded at least in part under heat and pressure without failure of film integrity, flexibility and resilience, between mold halves of a compression blow mold, at least one of the halves having internal cavities so that the outside surface layers of the sheets face the mold halves and the inside surface layers are positioned to contact each other when the mold is closed; and
  applying pressure and heat to the sheets in the closed mold while applying gas pressure to the portion of the sheets within the internal cavities of the mold to produce the film based structure.

4. A method for forming a film based assembly comprising: bonding a structure formed according to claim 3 to a plastic fluid transporting component.

5. A method for forming a film based assembly according to claim 4 wherein the plastic fluid transporting component is made from chlorine-free materials.

6. A method for forming a film based assembly according to claim 4 wherein the bonding is accomplished by applying a mixture of a polymeric binder and susceptor particles to the structure or component or both, contacting the structure and component together to form a joint at the location of bonding, and subjecting the joint to electromagnetic radiation.

7. A method for forming a film based assembly according to claim 4 wherein the bonding is performed by adhesive bonding.

8. A method for forming a film based assembly according to claim 7 wherein the adhesive used in the adhesive bonding contains susceptor particles, and further wherein the bonding step comprises subjecting the adhesive to electromagnetic radiation to enhance green strength of the adhesive.

9. A film based assembly according to claim 1, wherein the Young's moduli of the second and third thermoplastic polymers are up to about three times the Young's modulus of the first thermoplastic polymer.

10. A film based assembly according to claim 1, wherein the flexibility of the first thermoplastic polymer is measured by its Young's modulus within a range of about 10 to about 60 megaPascals, and wherein the Young's moduli of the second and third thermoplastic polymers are within a range of from about 15 to 300 megaPascals.

11. A film based assembly according to claim 1, wherein said film has an outside surface abrasion resistance having an abrasive index range of at least about 100 as measured by ASTM test D1630-83.

12. A film based assembly according to claim 1, wherein the outside and inside surface layers are contiguously united with the core layer, and wherein the thickness ratio of the sum of the outside and inside surface layers to the core layer is between about 2:1 to about 1:15.

13. A film based assembly according to claim 1, wherein the molded structure is bonded to at least one length of a chlorine-free polymeric tube.

14. A film based assembly according to claim 1, wherein the flexibility of the first thermoplastic polymer is measured by its Young's modulus within a range of about 10 to about 60 megaPascals; wherein the Young's moduli of the second and third thermoplastic polymers are within a range of from about 15 to 300 megaPascals; wherein the outside and inside surface layers are contiguously united with the core layer; wherein the thickness ratio of the sum of the outside and inside surface layers to the core layer is between about 2:1 to about 1:15; and wherein the first, second and third thermoplastic polymers are polymers of olefin monomers selected from the group consisting of C2 to C4 mono-unsaturated alkenes or are copolymers of said olefin monomers and substituted olefin monomers selected from the group consisting of C4 to C14 mono-unsaturated alkene, a C8 to C14 aryl alkene, or a C2 to C6 mono-unsaturated alkene having a moiety selected from the group consisting of acetoxy, carboxy, oxyalkanoyl, and alkoxycarbonyl of 1 to 6 carbons in the alkoxy group.

15. A method of forming a film based structured according to claim 3, wherein the flexibility of the first thermoplastic polymer is measured by its Young's modulus within a range of about 10 to about 60 megaPascals; wherein the Young's moduli of the second and third thermoplastic polymers are within a range of from about 15 to 300 megaPascals; the outside and inside surface layers are contiguously united with the core layer; and wherein the thickness ratio of the sum of the outside and inside surface layers to the core layer is about 2:1 to about 1:15.

16. A method of forming a film based structure according to claim 15, wherein the first, second and third thermoplastic polymers are polymers of olefin monomers selected from the group consisting of C2 to C4 mono-unsaturated alkenes or are copolymers of said olefin monomers and substituted olefin monomers selected from the group consisting of C4 to C14 mono-unsaturated alkene, a C8 to C14 aryl alkene, or a C2 to C6 mono-unsaturated alkene having a moiety selected from the group consisting of acetone, carboxy, oxyalkanoyl, and alkoxycarbonyl of 1 to 6 carbons in the alkoxy group.

* * * * *

UNITED STATES PATENT AND TRADEMARK OFFICE
CERTIFICATE OF CORRECTION

PATENT NO.: 5,712,044

DATED: January 27, 1998

INVENTOR(S): Dan L. Fanselow et al.

It is certified that error appears in the above-identified patent and that said Letters Patent is hereby corrected as shown below:

On title page, item "[75] Inventors:", delete "Lester B. Odegaard, Afton;".

In column 38, line 26, in claim 16, delete "acetone" and insert - - acetoxy - -.

Signed and Sealed this

Twenty-first Day of April, 1998

Attest:

BRUCE LEHMAN

Attesting Officer

Commissioner of Patents and Trademarks